United States Patent [19]
Cannell et al.

[11] Patent Number: 6,013,250
[45] Date of Patent: Jan. 11, 2000

[54] COMPOSITION FOR TREATING HAIR AGAINST CHEMICAL AND PHOTO DAMAGE

[75] Inventors: David Cannell, New York, N.Y.; Nghi Nguyen, Middlesex, N.J.

[73] Assignee: L'Oreal S. A., Paris, France

[21] Appl. No.: 08/857,530

[22] Filed: May 16, 1997

Related U.S. Application Data

[63] Continuation-in-part of application No. 08/496,138, Jun. 28, 1995, Pat. No. 5,681,554.

[51] Int. Cl.$^7$ ..................................................... A61K 7/06
[52] U.S. Cl. ................. 424/70.51; 424/70.1; 424/70.14; 424/70.15; 424/70.24; 424/70.27; 424/70.28
[58] Field of Search ................................. 424/70.1–70.51

[56] References Cited

U.S. PATENT DOCUMENTS

| | | | |
|---|---|---|---|
| 3,958,581 | 5/1976 | Abegg et al. | 132/7 |
| 3,972,998 | 8/1976 | Keiner | 424/70 |
| 4,047,888 | 9/1977 | Papantoniou | 8/10.2 |
| 4,390,525 | 6/1983 | Yoshioka et al. | 424/71 |
| 4,495,173 | 1/1985 | Matsunaga et al. | 424/70 |
| 4,517,175 | 5/1985 | Iwabuchi et al. | 424/70 |
| 4,542,014 | 9/1985 | Bresak et al. | 424/70 |
| 4,604,282 | 8/1986 | Grollier et al. | 424/74 |
| 4,751,074 | 6/1988 | Matsunaga et al. | 424/70 |
| 4,839,168 | 6/1989 | Abe et al. | 424/74 |
| 4,935,230 | 6/1990 | Naito et al. | 424/70 |
| 4,970,067 | 11/1990 | Panandiker et al. | 424/70 |
| 5,009,813 | 4/1991 | Watanabe et al. | 252/545 |
| 5,071,960 | 12/1991 | Turowski et al. | 530/356 |
| 5,192,332 | 3/1993 | Lang et al. | 8/405 |
| 5,204,099 | 4/1993 | Barbier et al. | 424/401 |
| 5,213,792 | 5/1993 | Grundmann et al. | 424/70 |
| 5,286,406 | 2/1994 | Scholz et al. | 252/174.17 |

FOREIGN PATENT DOCUMENTS

| | | | |
|---|---|---|---|
| 0052943 | 6/1982 | European Pat. Off. | A61K 7/11 |
| 0057837 | 8/1982 | European Pat. Off. | A61K 7/06 |
| 0099780 | 2/1984 | European Pat. Off. | C08H 1/06 |

OTHER PUBLICATIONS

Zviak, Charles, *The Science of Hair Care*, pp. 116–125 (1987).
Flick, Ernest W., *Cosmetic and Toiletry Formulations*, vol. 2, 2$^{nd}$ Ed., pp. 456–457 (1992).
Database "Chemical Abstracts" (Host:Stn) Abs. 124: 269 956, Colmbus, OH, USA; JP 08 020 518 A (Shiseido Co., Ltd) Jan. 23, 1996 XP–002056951.
Database "Chemical Abstracts" (Host: Stn) Abs. 124: 211 493, Colombus, OH, USA; JP 07 330 560 A (Shiseido Co., Ltd) Dec. 19, 1995 XP–002056950.

*Primary Examiner*—Thurman K. Page
*Assistant Examiner*—Alysia Berman
*Attorney, Agent, or Firm*—Baker & Botts, LLP

[57] ABSTRACT

The present invention relates to a hair treatment composition which provides an excellent finishing effect and superior protection against environmental, chemical, and grooming-associated damage. The compositions of the present invention comprise hydrolyzed protein having an abundance of anionic amino acids and in particular, sulphur-containing amino acids, as well as divalent cationic compounds, such that the anionic components of the hydrolyzed protein may effectively bind to the hair by means of cationic bridges. While bound to the hair, the sulphur containing amino acids in the hydrolyzed protein may serve as "decoys" for the effects of a variety of damaging agents. Compositions of the present invention may further comprise a vitamin compound which enhances these protective benefits.

15 Claims, 12 Drawing Sheets

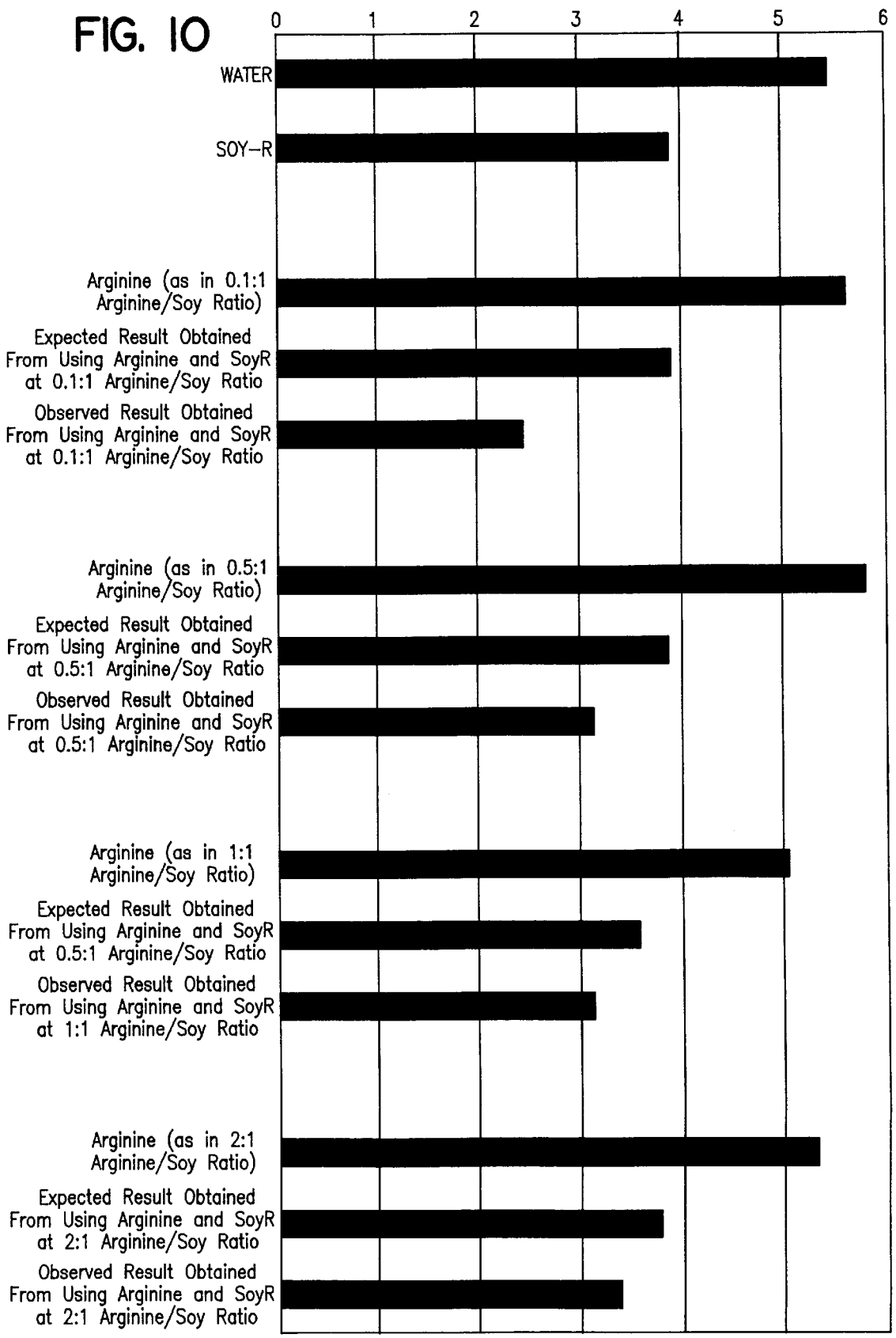

COMPOSITION FOR TREATING HAIR AGAINST CHEMICAL AND PHOTO DAMAGE

CROSS REFERENCE TO RELATED APPLICATIONS

The present application is a continuation-in-part of Ser. No. 08/496,138, filed Jun. 28, 1995 now U.S. Pat. No. 5,681,554.

I. INTRODUCTION

The present invention relates to a hair treatment composition which provides an excellent finishing effect and superior protection against environmental, chemical and grooming-associated damage. The compositions of the present invention comprise hydrolyzed protein having an abundance of anionic amino acids and in particular, sulphur-containing amino acids, as well as divalent cationic compounds, such that the anionic components of the hydrolyzed protein may effectively bind to the hair by means of cationic bridges. While bound to the hair, the sulphur containing amino acids in the hydrolyzed protein may serve as "decoys" for the effects of a variety of damaging agents. The compositions of the present invention may further comprise a vitamin compound which enhances these protective benefits.

BACKGROUND OF THE INVENTION

Human hair is comprised of keratin ("hair keratin"), a tough fibrous protein having a high sulfur content. Hair keratin is routinely exposed to a variety of activities that compromise its structure. For example, simple grooming and styling results in loss of cuticle scale, subjecting the hair's inner cortex to further damage and eventually leading to hair breakage. Shampooing causes frictional damage to cuticle scale and extracts hair protein. Ultraviolet light from the sun reduces the hair's mechanical strength and causes fading of natural and applied hair color. Exposure to chlorinated water in swimming pools causes oxidation of hair keratin, leading to increased protein loss during combing and brushing.

These practices are less damaging to hair than direct exposure to the reactive chemicals commonly used by hair stylists, such as permanent wave agents, hair colors, bleaches, straighteners, peroxides, thio solutions, sodium hydroxide and the like. However, the cumulative effects of daily cleansing, grooming, and ultraviolet light are far greater than the damage associated with the above-mentioned chemicals. However, if hair has been chemically treated, then daily grooming, shampooing and sun exposure has an even greater potential for causing extensive damage.

In view of the above, there is a need for a novel class of hair treatment compositions which provide not only beautifying effects to damaged and non-damaged hair, but also provide superior protection from the various activities mentioned above that compromise hair structure.

SUMMARY OF THE INVENTION

The present invention relates to a composition comprising an effective amount of an anionic hydrolyzed protein containing an abundance of sulphur-containing amino acids, which effectively binds to the anionic surface of hair via divalent cationic bridges. Such a composition, when applied to the hair, reduces hair damage and protein loss caused by grooming, excessive heat, chlorinated water, ultraviolet light from the sun, and reactive chemicals. The addition of a vitamin compound which has antioxidant and/or ultraviolet absorbent properties further enhances the protective efficacy of the compositions of the present invention.

In particular, the present invention provides for a hair treatment composition comprising:

(a) from about 0.1 to about 50% by weight of a hydrolyzed protein, wherein the molar ratio of anionic amino acids to cationic amino acids is at least about 1.1 to 1.0, and wherein the hydrolyzed protein has an average molecular from about 200 to 500,000 daltons and comprises at least 0.25% by weight of sulphur-containing amino acids;

(b) a divalent cationic compound, wherein the molar ratio of said compound to the anionic amino acids of the hydrolyzed protein is from about 0.2:1 to about 4:1;

(c) optionally from about 0.01 to about 5% by weight of a vitamin compound, wherein the vitamin compound absorbs ultraviolet light within the wavelength region between 290 nm and 420 nm and/or is effective in retarding oxidation of hair; and (d) from about 1 to 99.89% by weight of a cosmetic carrier.

BRIEF DESCRIPTION OF THE DRAWINGS

FIG. 10 is a bar graph illustrating the change in color of irradiated hair swatches treated with solution containing varying molar ratios of dibasic cationic amino acid compounds to hydrogen protein.

DETAILED DESCRIPTION OF THE INVENTION

Figure 1A:
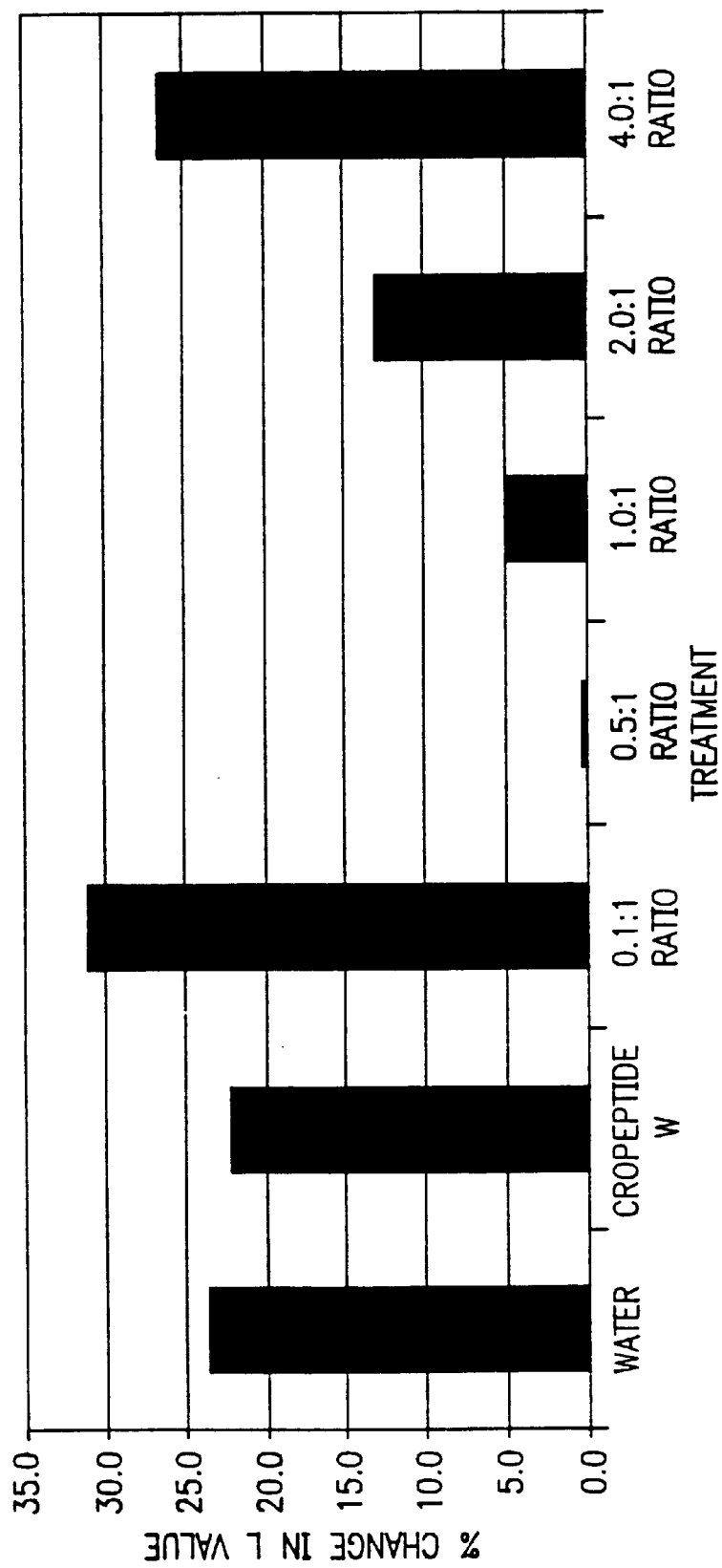
FIG. 1a is a bar graph illustrating the change in lightness of irradiated hair swatches treated with solutions containing varying molar ratios of divalent cationic compounds to hydrolyzed protein from wheat.
Figure 1B:
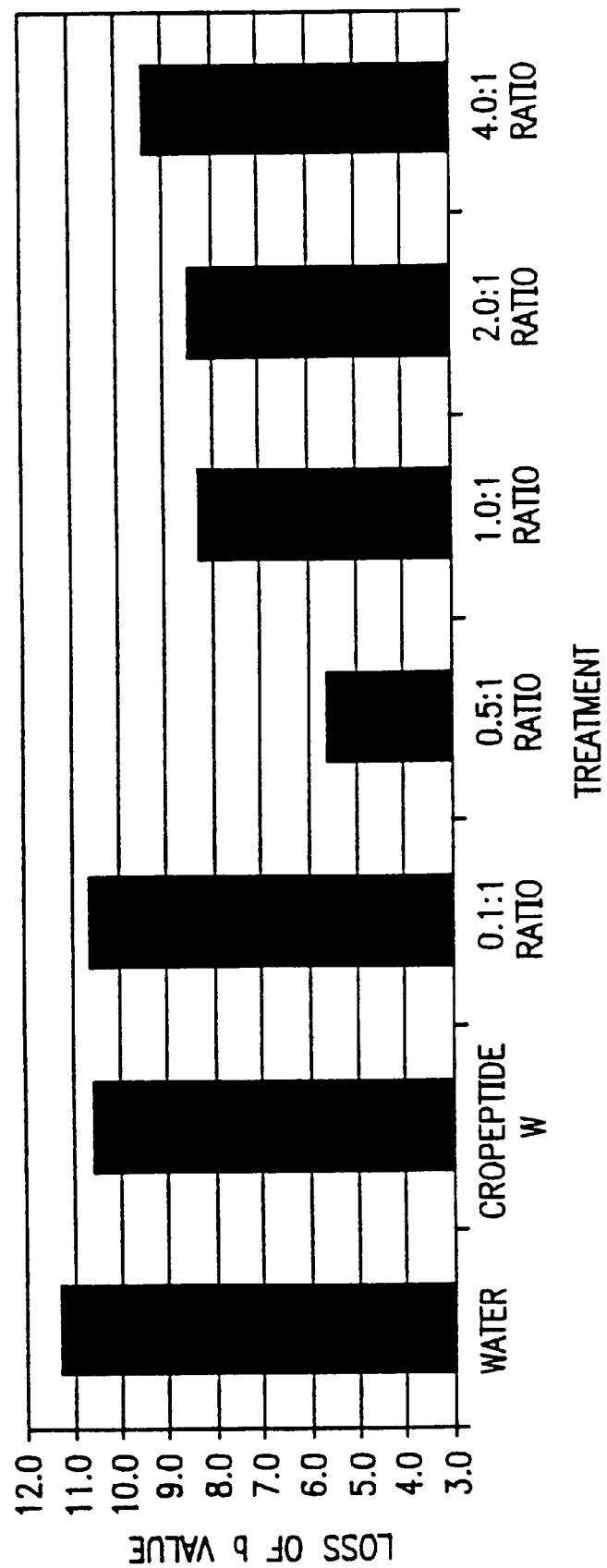
FIG. 1b is a bar graph illustrating the change in color of irradiated hair swatches treated with solutions containing varying molar ratios of divalent cationic compounds to hydrolyzed protein from wheat.
Figure 1C:
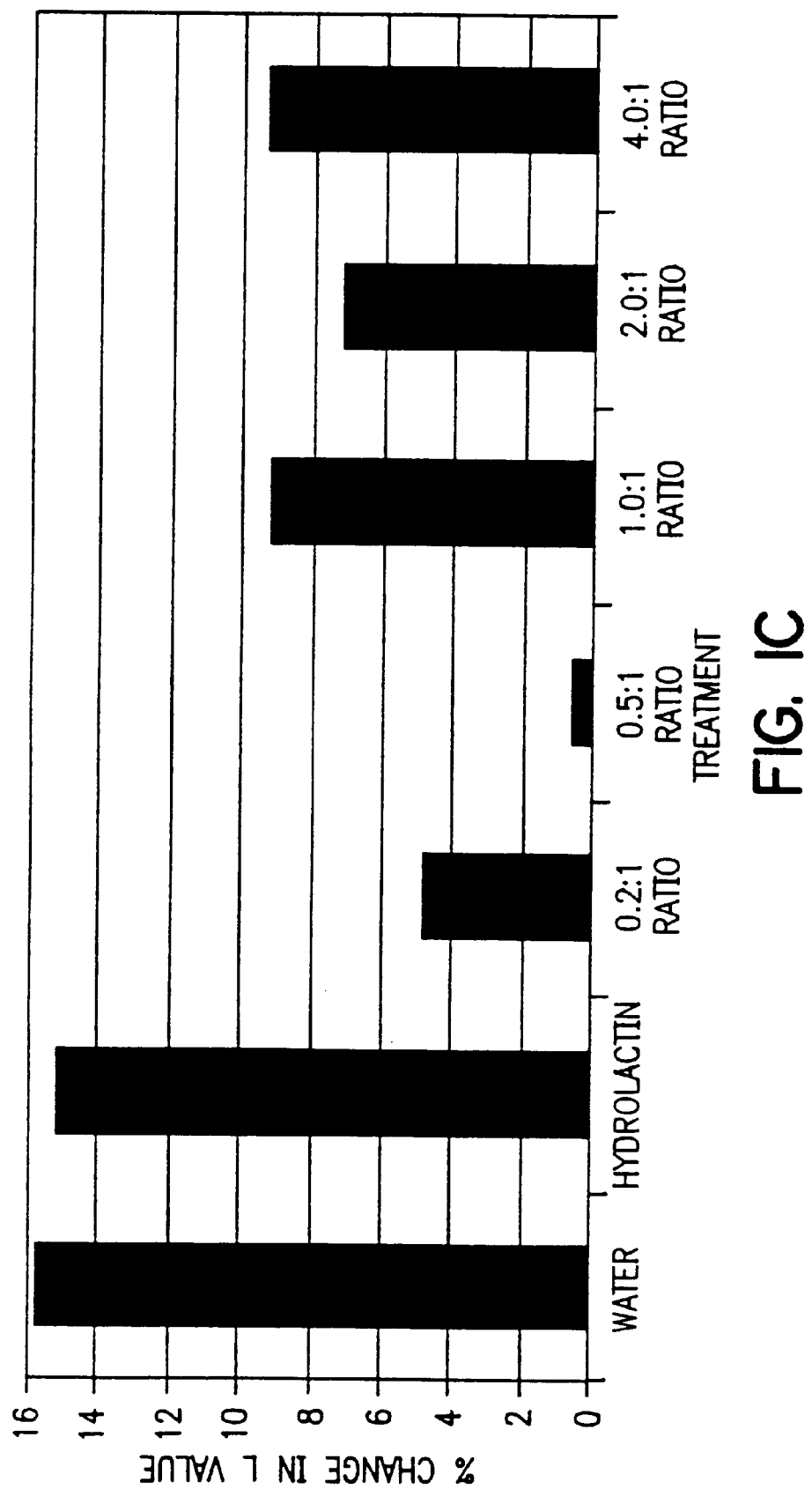
FIG. 1c is a bar graph illustrating the change in lightness of irradiated hair swatches treated with varying molar ratios of divalent cationic compounds to hydrolyzed protein from milk.
Figure 1D:
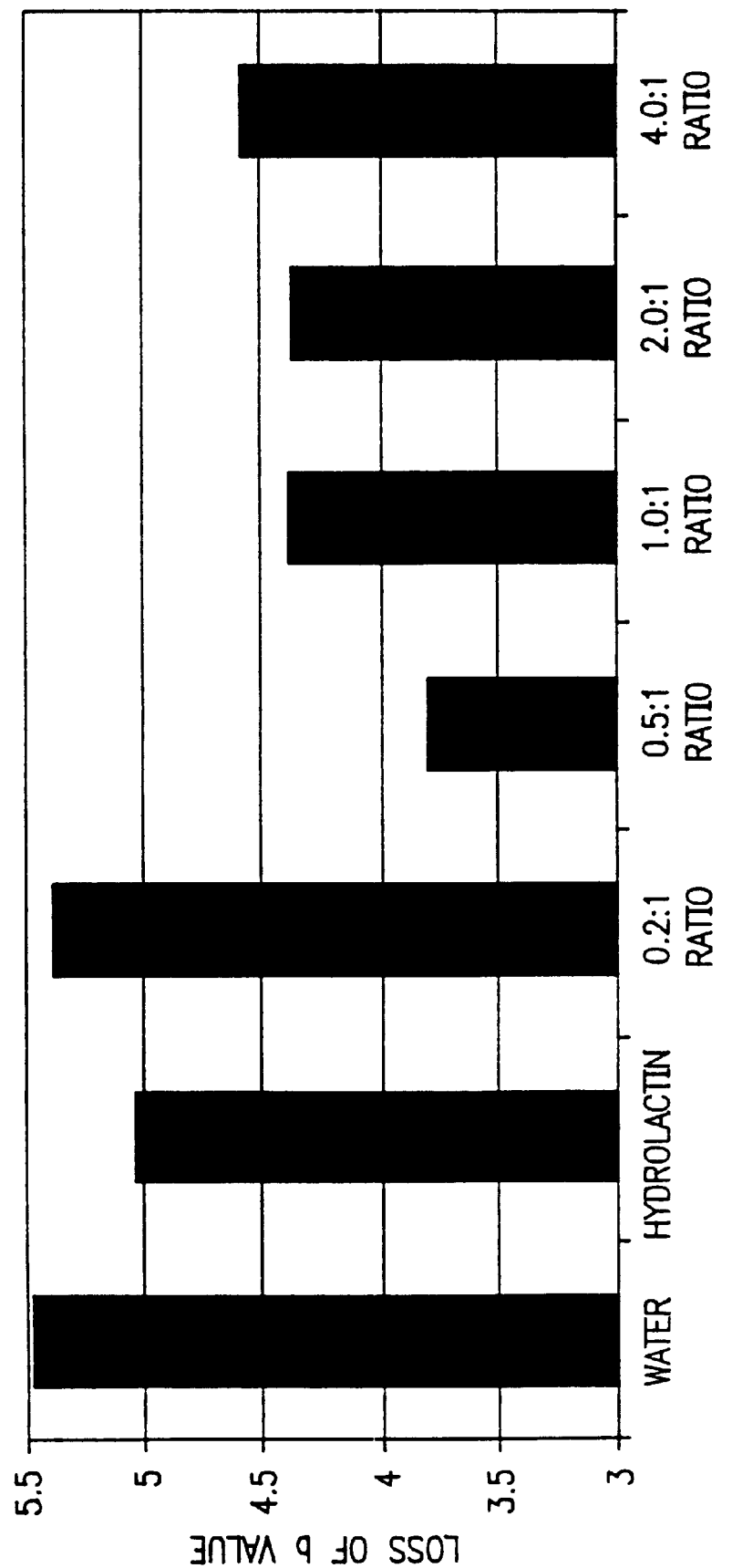
FIG. 1d is a bar graph illustrating the change in color of irradiated hair swatches treated with varying molar ratios of divalent cationic compounds to hydrolyzed protein from milk.

The present invention relates to compositions for treating hair which protect hair from photo damage, chemical damage and protein loss due to grooming activities including, but not limited to, combing, brushing, blow drying, curling and the like. Such compositions of the invention comprise a hydrolyzed protein, a divalent cationic compound, and preferably a vitamin compound, in a cosmetic carrier.

The compositions according to the present invention include, but are not limited to, shampoos, conditioners, hair treatment creams, styling gels, mousse, pump hair sprays and aerosol hair sprays, set lotions, blow styling lotions, hair color lotions, hair relaxing compositions, permanent wave first agents, and permanent wave second agents.

The amount of hydrolyzed protein in these compositions is dependent on various considerations, such as product esthetics and the type of commercial product end-use desired, for example, as a shampoo, cream or treatment conditioner for normal hair, oily hair, dry hair, permed hair, thick hair, fine hair, etc. The considerations regarding the appropriate amount of hydrolyzed protein to be used in view of the end-use would be known to those of ordinary skill in the art. In this regard, products such as shampoos utilize relatively less hydrolyzed protein, generally in the range of 0.1–1.0% by weight of the composition, as the substantivity from shampoos is lower due to their detergency. High concentrations of protein in shampoos tend to adversely affect foam characteristics, and excess protein is merely washed away during rinsing. However, treatment products designed to build strength into the hair have longer hair contact times and high concentrations of protein are utilized to favor absorption. Such compositions may contain up to 50% by weight of hydrolyzed protein.

Thus, compositions of the present invention comprise from about 0.1 to 50.0% by weight, preferably from about 0.1 to 10.0% by weight, and more preferably from about 0.1 to 4.0% by weight of a hydrolyzed protein.

The term "hydrolyzed protein," as used herein, refers to the product of the hydrolysis of homogeneous or heterogeneous proteins, or their respective components, derivatives or combinations thereof, from sources including, but not limited to, plants and their respective components, seeds, animal bones, connective tissue, animal keratin, bovine and porcine collagen, human hair, wool, silk, elastin, reticulin, milk, egg, wheat, corn, soya, oats, casein, albumin, or any collagenous or keratinic substance, or derivatives thereof. With respect to the compositions of the present invention, there is no restriction on the source of protein, protein components or derivatives, provided that the hydrolyzate has the desired physical properties described herein. However, preferred protein sources include keratin, soya, milk, collagen, wheat and their respective components, derivatives or combinations thereof. Additional preferred protein sources may be identified as proteins having desirable amino acid compositions, as set forth below. Suitable derivatives include proteins chemically modified to alter their ionic charge, for example, by sulfonation or succinylation.

The compositions of the present invention are not limited to hydrolyzed proteins produced from naturally occurring proteins. Synthetic proteins, peptides, or amino acids as well as naturally occurring proteins, peptides or amino acids or mixtures of naturally occurring and synthetic proteins and/or peptides and/or amino acids may also be used according to the invention. Hydrolyzed protein prepared from various proteins, their respective components, and derivatives may be combined and used in the composition of the present invention. Moreover, a hydrolyzed protein may be supplemented by the addition of one or more natural or synthetic peptides or amino acids to achieve the ionic characteristics or sulphur content discussed below.

Methods for producing hydrolyzed proteins from the above-mentioned protein sources include, but are not limited to: 1) acid hydrolysis; 2) alkali hydrolysis; and 3) enzyme hydrolysis using a suitable protease. These methods, along with several others, for preparing hydrolyzed proteins are well known in the art. Further, hydrolyzed proteins suitable for the compositions of the present invention are commercially available.

Hydrolyzed proteins typically have an average molecular weight from about two hundred to several hundred thousand daltons, depending on the nature of the protein and/or the extent of hydrolysis. While hydrolyzed proteins of low molecular weight favor absorption, they are more easily lost from the hair by subsequent washing. On the other hand, proteins of very high molecular weight do not penetrate well. Generally, an average molecular weight of 500,000 daltons or less is desirable for hydrolyzed proteins utilized in this invention.

Therefore, in particular embodiments of the present invention, the average molecular weight of the hydrolyzed protein is from about 200 to 500,000 daltons, preferably from about 200 to 100,000 daltons, more preferably from about 200 to 50,000 daltons, and even more preferably from about 200 to 20,000 daltons.

In still further embodiments of the invention, the above-mentioned proteins or their derivatives, synthetic peptides, natural peptides or combinations thereof, may be comprised in the composition of the present invention without any additional hydrolysis treatment, provided that the desired molecular weight, ionic characteristics and sulphur content set forth below may be achieved.

Every protein molecule can be considered as a polymer of amino acids. There are 20 naturally occurring varieties of amino acid, each with a common backbone combined with one of 20 variable side chains. Amino acids are commonly classified as either neutral, anionic or cationic amino acids based on the charge of the variable side chain.

The naturally occurring anionic amino acids include aspartic acid and glutamic acid, both of which have a carboxylate group at the termini of their respective variable side chains. The present invention also provides for amino acids modified such that the net charge of the amino acid is made anionic, or if the net charge is already anionic, such charge may be increased. Examples of such modifications include, but are not limited to, succinylation or sulfonation of the amino acid. All such amino acids are considered, herein, to be "anionic amino acids."

The naturally occurring cationic amino acids include lysine, arginine and histidine, all of which comprise an amino group in their respective variable side chains. Amino acids may also be modified to result in a net cationic charge. All such amino acids are considered herein to be "cationic amino acids".

Hair care products are generally in the pH range of 2.0 to 10.0. Proteins having a predominance of anionic amino acids, relative to cationic amino acids, are likely to be negatively charged at the general pH range of hair care products. Conversely, proteins having a relative abundance of cationic amino acids are likely to be positively charged under similar conditions.

It is preferred that the amino acid composition of the hydrolyzed protein in the present invention contain a predominance of anionic amino acids relative to cationic amino acids, so that the hydrolyzed protein at the general pH range of hair care products is negatively charged.

Specifically, the composition of the present invention preferably comprises a hydrolyzed protein, wherein the molar ratio of anionic amino acids to cationic amino acids is at least 1.1:1, preferably from about 1.1:1 to 1.1:1 to 25:1, and more preferably from about 1.1 to 1.1:1 to 15:1.

The term "molar ratio of anionic amino acids to cationic amino acids" of the hydrolyzed protein in the present invention means the total molar amount of anionic amino acids (for example, adding the individual molar amount of the anionic amino acids, such as aspartic acid and glutamic acid) in relation to the total molar amount of cationic amino acids (for example, adding the individual molar amount of lysine, arginine and histidine) in the hydrolyzed protein.

The molar ratio of anionic amino acids to cationic amino acids may be readily calculated based on the overall amino acid composition of the hydrolyzed protein or mixtures of hydrolyzed proteins. Such compositions are frequently known in the art. Alternatively, the amino acid composition of any protein may be determined using techniques known to those skilled in the art, which include, but are not limited to, (1) automated amino acid analysis and (2) high pressure liquid chromatography. Such techniques separate the individual amino acids, and the molar ratio of anionic to cationic amino acids may be determined.

Further, the hydrolyzed protein of the present invention is characterized in that it comprises at least 0.25%, preferably from about 0.25 to 15%, and more preferably from about 0.25 to 5.0% by weight of a sulphur containing amino acid. The "term sulphur-containing amino acid" as used herein refers to any amino acid, natural or synthetic, containing sulphur in any form, including, but not limited to, sulphydryl groups or disulphide bonds. Sulphur-containing amino acids suitable for the present invention include, but are not limited to, cysteine, cystine, methionine, and their respective derivatives and synthetic analogues. Compositions according to the present invention may, in particular embodiments, comprise in addition to the protein hydrolyzate, sulphur-containing compounds such as amino acids or sulphur-containing salts which may supplement the amount of sulphur in the composition to achieve the percentages (by weight, relative to the hydrolyzed protein) set for the above.

Comparative tests that have been carried out, and are described below, suggest that the sulphur-containing amino acids in the hydrolyzed protein shield the hair from various assaults, such as exposure to ultraviolet light or chemicals known to cause hair damage. Without being bound by any theory, it is believed that the sulphur-containing amino acids act as a buffer or "decoy" between the hair and the assaulting agent.

For example, sunlight and certain chemical agents damage hair by breaking naturally occurring disulphide bonds. Applying proteins comprising sulphur-containing amino acids to hair provides more sulphur bonds, particularly disulphide bonds, for breakage by exposure to sunlight or chemical treatments, thus leaving the sulphur bonds occurring naturally in the hair less vulnerable to such assaults.

In that regard, additional compounds having sulphydryl groups or disulphide bonds may be added to the compositions of the present invention to enhance protection from oxidation and ultra-violet light. For example, free residual cystine, such as cystine diester hydrochloride or any other sulphur-containing salt, may be added to increase the content of disulphide bonds present in the composition. Alternatively, peptide fragments rich in sulphur-containing amino acids or any other compound having sulphydryl groups or disulphide bonds may be used in the present invention.

Synthetic or naturally occurring proteins and hydrolyzed proteins suitable for the present invention can be readily prepared from appropriate sources, or, alternatively, purchased commercially.

Table 1 sets forth relevant characteristics of nonlimiting examples of preferred protein sources from which the hydrolyzed proteins of the present invention may be prepared. These proteins were purchased from Croda, Inc. of Edison, N.J.

TABLE 1

| Brand Name | Protein Source | MW | % Cystine | Molar Ratio (anionic/cationic amino acids) |
|---|---|---|---|---|
| Crotein WKP | Hydrolyzed protein from keratin | 600 | 10.22 | 1.1:1 |
| Hydrosoy 2000/SF | Hydrolyzed protein from soy | 1,000 | 1 | 2.2:1 |
| Hydrolactin 2500 | Hydrolyzed protein from milk | 2,500 | 0.4* | 2.19:1 |
| Crotein SPA,O,C | Hydrolyzed protein from collagen | 10,000 | 0.5 | 1.6:1 |
| Hydrotriticum 2000 | Hydrolyzed protein from wheat | 3,000 | 1.80 | 6.2:1 |
| Cropeptide W | Hydrolyzed protein from wheat | 2,500 | 1.40 | 13.9:1 |

*Cysteine

Hair care products are generally in the pH range of 2.0 to 10.0, although products for shampooing, conditioning and treatment of the hair are more generally in the range of 3.5 to 10.0, and even more typically between the pH of about 3.5 and 8.0. At a pH greater than 3.8, the surface of the hair fiber has a predominance of negative charges, so that the divalent cationic compound is more effective at assisting with protein binding. In this regard, the preferred pH of the composition of the present invention is between 2.0 to 10.0, preferably from about 3.5 to about 10.0, and more preferably from about 3.5 to about 8.0.

The compositions of the invention also comprise a divalent cationic compound, for example, a divalent mineral cation, including, but not limited to, divalent calcium, copper, magnesium, manganese, iron, strontium, zinc, cadmium, barium, silver, nickel, cobalt or mercury. The divalent mineral may preferably be obtained from an ionic salt, including, but not limited to, salts formed with carboxylate, sulfonate, phosphate, halide, carbonate, silicate, nitrate, or pantothenate ions.

Further, divalent non-mineral compounds may be used in the composition of the present invention, including, but not limited to, a peptide that comprises at least two cationic amino acids, such as, for example, histidine, arginine, lysine, orinithine hydroxylysine, their respective derivatives, analogues or combinations thereof, such that the peptide has a net divalent cationic charge. The divalent cationic charge may result from the presence of cationic amino acids of a single type, or multiple types. Such a peptide may comprise from at least 2 to about 200 amino acids, preferably between 2 to 10 amino acids. The molar ratio of the divalent non-mineral compound to anionic amino acids of the hydrolyzed protein is at least 0.2:1 to 4:1, preferably between about 0.5:1 to 1:1, and more preferably about 0.5:1. Stated another way, the ratio of the cationic amino acids of the divalent non-mineral compound to the anionic amino acids of the hydrolyzed protein is at least 0.4:1 to 8: 1, preferably between about 1:1 to 2: 1, and more preferably at about 1:1.

Additionally, peptides having a net cationic charge greater than 2 may be used in the composition of the present invention, including, but not limited to , a peptide that comprises at least two cationic amino acids, such as, for example, histidine, arginine, lysine, orinithine hydroxylysine, their respective derivatives, analogues or combinations thereof. Such a peptide may comprise from at least 2 to about 200 amino acids, preferably between 2 to 10 amino acids. The ratio of the cationic amino acids of the peptide to the anionic amino acids of the hydrolyzed protein is at least 0.4:1 to 8:1, preferably between about 1:1 to 2:1, and more preferably at about 1.0:1.

Other divalent non-mineral substances which may be used in the compositions of the present invention, include, but not are not limited to, diamino compounds having the general formula:

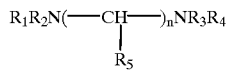

Wherein n=1–6 and $R_1$, $R_2$, $R_3$, $R_4$, and $R_5$, which may be the same or different, may be a hydrogen or an alkyl group, including but not limited to, a methyl, ethyl, isopropyl, butyl, or propyl group, such that the compound has a net divalent cationic charge. The molar ratio of the diamino compound to the anionic amino acids of the hydrolyzed protein is at least 0.2:1 to 4:1, preferably between about 0.5:1 to 1:1, and more preferably at about 1:1. Stated another way, the ratio of the amino groups of the diamino compound to the anionic amino acids of the hydrolyzed protein is at least 0.4:1 to 8:1, preferably between 1.0:1 to 2:1, and more preferably at about 1:1.

Other cationic polyamino compounds which may be used in the compositions of the present invention include compounds having at least three amino groups. Such cationic polyamino compounds may include compounds having the general formula:

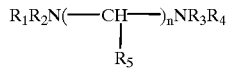

Wherein n=1–6 and $R_1$, $R_2$, $R_3$, $R_4$, and $R_5$, which may be the same or different, may be a compound comprising one or more amino groups or a hydrogen or an alkyl group, including but not limited to, a methyl, ethyl, isopropyl, butyl, or propyl group. The ratio of the amino groups of the cationic polyamino compound to the anionic amino acids of the hydrolyzed protein is between about 0.4:1 to 8:1, preferably between about 1.0:1 to 2:1, and more preferably about 1:1. Examples of such compounds which may be used in the present invention, include, but are not limited to, polyethylenimine, $(C_2H_5N)_n$, where n=from about 1–100, or greater. One brand-name of this compound is POLYMINEPEI®, sold by BASF of New Jersey. Its molecular weight is between about 800 to 750,000. Another compound comprising at least three amino groups and which may be used in the present invention includes polyamidoamine. Such compound is sold under the brand-name STARBURST PAMAM by Dendritech, Inc. of Michigan.

Other polyamino cationic compounds which may be used in the compositions of the present invention include cationic amino acid compounds. The term "cationic amino acid compound," as used in the specification and claims, is defined to include within the scope of that term any amino acid having an amino group in its variable side chain, such as, for example, histidine, lysine, arginine, hydroxylysine, ornithine, their respective derivatives, analogues, and stereoisomeric configurations or combinations thereof. Derivatives of the cationic amino acid compound may include salt forms of the amino acid. For example, the cationic amino acid of the present invention may comprise a salt selected from the group consisting of hydrochloride, hydrochloride monohydrate, monohydrochloride, monohydrate, methyl ester dihydrochloride, dihydrochloride, ethyl ester dihydrochloride or combinations thereof.

Specific cationic amino acid compounds which may be suitable for the present invention include the following:

| Arginine | |
|---|---|
| Arginine aspartate | DL-Arginine hydrochloride monohydrate |
| Arginine PCA | D-Arginine monohydrochloride |
| L-Arginine | L-Arginine monohydrochloride |
| DL-Arginine | L-Homoarginine hydrochloride |
| D-Arginine hydrate | |
| D-Arginine hydrochloride | |
| L-Arginine hydrochloride | |
| L-Arginine methyl ester dihydrochloride | |

| Histidine | |
|---|---|
| D-Histidine | L-Histidine methyl ester dihydrochloride |
| L-Histidine | D-Histidine monohydrochloride monohydrate |
| DL-Histidine | L-Histidine monohydrochloride monohydrate |
| | DL-Histidine monohydrochloride monohydrate |

| Lysine | |
|---|---|
| Lysine | L-Lysine dihydrochloride |
| DL-Lysine | L-Lysine monohydrate |
| L-Lysine | DL-Lysine dihydrochloride |
| D-Lysine | L-Lysine ethyl ester dihydrochloride |
| Lysine aspartate | |
| Lysine PCA | |
| L-Lysine, compound, with 5-oxo-L-proline (1:1) | |
| D-Lysine hydrate | |
| L-Lysine hydrate | |
| DL-Lysine monohydrochloride | |
| D-Lysine monohydrochloride | |
| L-Lysine monohydrochloride | |

| Hydroxylysine | |
|---|---|
| 5-Hydroxy-DL-lysine hydrochlordie | |
| 5-Hydroxy-L-lysine dihydrochloride monohydrate | |

-continued

5-Hydroxylysine hydrochloride
Ornithine
D-Ornithine hydrochloride
L-Ornithine hydrochloride
L-Ornithine dihydrochloride
D-Ornithine monohydrochloride
L-Ornithine monohydrochloride The molar ratio of the cationic amino acid compound to anionic amino acids of the hydrolyzed protein is at least 0.2:1 to 4:1, preferably between about 0.5:1 to 1:1, more preferably at about 0.5:1. Stated another way, the ratio of the amino groups of the cationic amino acid compound to anionic amino acids of the hydrolyzed protein is at least 0.4:1 to 8:1, preferably between about 1.0 and 2:1, and more preferably at about 1:1.

It is desirable that the molar ratio of divalent compound to the anionic amino acids of the hydrolyzed protein is effective in "bridging" the hydrolyzed protein to the hair to form a hydrolyzed protein layer, wherein said layer is effective in at least partially protecting the hair from photo damage, oxidation and grooming-associated damage. In this regard, the preferred molar ratio of divalent cationic compound to anionic amino acids of the hydrolyzed protein is between about 0.2:1 to 4:1, preferably between about 0.5:1 to 1:1, and more preferably at about 0.5:1.

Examples 1–5, below, demonstrate the correlation between the molar ratio of divalent cationic compound to the anionic amino acids of the hydrolyzed protein and the protective effects of the compositions of the present invention.

The composition of the invention may further comprise from about 0.01 to 5% by weight of a vitamin compound or its respective derivative which functions as an antioxidant and/or absorbs ultraviolet light. Preferably, the antioxidant vitamin is more readily oxidized than hair and hence can retard or inhibit the oxidation of the hair when applied. The vitamin compound may alternatively or additionally absorb ultra-violet light within the wavelength region between 290 and 420 nm, such that the vitamin may protect hair from photo damage when comprised in a composition of the invention.

Suitable vitamin compounds and their respective derivatives falling within the scope of the present invention include, but are not limited to, the following:

| Vitamin | Derivative |
| --- | --- |
| Vitamin A (Retinol) | Retinyl Palmitate |
| Pro Vitamin A (Beta-Carotene) | |
| Vitamin $B_1$ (Thiamine) | Thiamine Nitrate |
| | Thiamine Phosphoric Acid Ester |
| Vitamin $B_3$ (Niacinamide) | Niacinamide Ascorbate |
| Vitamin $B_5$ (Pantothenic Acid) | |
| Vitamin $B_6$ (Pyridoxine) | Pyridoxine Dilaureate |
| | Pyridoxine Dioctenoate |
| | Pyridoxine Dipalmitate |
| | Pyridoxine Tripalmitate |
| Vitamin $B_{12}$ (Cyanocobalamin) | |
| Vitamin C (Ascorbic Acid) | Ascorbyl Palmitate |
| | Ascorbyl Glucoseamine |
| | Ascorbyl Dipalmitate |
| | Ascorbyl Stearate |
| Vitamin $D_2$ (Ergocalciferol) | |
| Vitamin $D_3$ (Cholecalciferol) | |
| Vitamin E (Tocopherol) | Tocopheryl Acetate |
| | Tocopheryl Linoleate |
| | Tocopheryl Nicotinate |
| | Tocopheryl Succinate |
| Vitamin F (Linoleic, Linolenic acids) | |
| Vitamin $K_1$ (Phylloquinone) | |

The above-mentioned vitamin compounds and their respective derivatives absorb ultra-violet light within the wavelength region between 290 and 420 nm.

Vitamin compounds and their respective derivatives (including, for example, salt or esterfied forms of the vitamin) may be combined and used in the composition of the present invention.

Examples 6–11, below, demonstrate that applying a composition comprising an anionic hydrolyzed protein comprising sulphur-containing amino acids, a divalent cationic compound and a vitamin compound to the hair provides substantial protection from photo damage, chemical damage and damage caused by grooming.

The composition of the present invention comprises from about 1 to 99.89% by weight of a cosmetic carrier. The term "cosmetic carrier" as used herein means the components, other than hydrolyzed protein, divalent cationic compound and vitamin compound, which are generally used in the cosmetic compositions within the scope of the present invention. Such cosmetic compositions may include, but are not limited to, shampoos, conditioners, hair treatment creams, styling gels, mousse, pump hair sprays and aerosol hair sprays and foams, set lotions, blow styling lotions, hair color lotions, hair relaxing compositions, permanent wave first agents, and permanent wave second agents.

Specifically, cosmetic carriers, as defined herein, include, but are not limited to, water, aqueous solutions, detergents, emollients, surfactants, foam boosters, thickeners, fatty esters, ethers, alcohols, polymers, preservatives, color, dyes, fragrance and other ingredients known to those skilled in the art.

Various specific examples of compositions of the present invention were tested for beautifying effects and performance by skilled hairdressers. Based on such tests, the compositions were found to impart an excellent look, smoothness, feel and shine to the hair, as well as to provide excellent comability under wet and dry conditions. It was also observed that the compositions of the present invention made the hair more manageable, indicating that such compositions were effective as moisturizing, softening and bodifying treatments.

Hair may be treated with the compositions of the present invention by applying effective amounts to the hair. When the composition of the present invention is present in the form of a shampoo or conditioner, the application is usually followed by rinsing the hair with water and finally drying the hair. When the composition of the present invention is a conditioner, treatment cream, styling gel or mousse, it may alternatively be retained in the hair or rinsed.

Further, the compositions of the present invention may be separated and applied to the hair in effective amounts by applying such amounts in multiple steps to treat the hair as may be practiced with such products as perm waves, hair straighteners and hair relaxers. For example, the protein and divalent cationic compound may be in the waving solution and the vitamin compound applied as a separate step before neutralizing the hair.

Many features of the invention will become apparent in the course of the following description of the exemplary embodiments which are given for illustration of the invention and are not intended to be limiting thereof.

The term "polyamino cationic agent," as recited in the specification and claims, is defined to include within the scope of that term any positively charged compound having a plurality of positively charged amino groups including, but not limited to, the compounds referenced in the specification and claims.

EXAMPLE 1

Effective Molar Ratios of Divalent Cationic Compound to Anionic Amino Acids in the Hydrolyzed Protein Bleached hair swatches were colored with an oxidation dye, o-Cl-p-Phenylenediamine sulfate/m-Phenylenediamine ("o-Cl-PPD/MPD"), and then treated with one of the following solutions for 10 minutes at 40° C.:

a) water
b) 3% by weight of hydrolyzed protein from wheat (Cropeptide W);
c) 3% by weight of hydrolyzed protein from wheat (Cropeptide W), wherein the molar ratio of the divalent cationic compound to anionic acidic amino acids in the hydrolyzed protein was either 0.1:1, 0.5:1, 1.0:1, 2.0:1 or 4.0:1.

In addition, bleached hair swatches were colored with an oxidation dye, o-Chloro-p-Phenylenediamine sulfate/4-Ethoxy-m-phenylenediamine sulfate ("o-Cl-PPD/DAPS") and then treated with one of the following solutions for 10 minutes at 40° C.:

a) water
b) 4% by weight of hydrolyzed protein from milk (Hydrolactin);
c) 4% by weight of hydrolyzed protein from milk (Hydrolactin), wherein the molar ratio of the divalent mineral to anionic acidic amino acids in the hydrolyzed protein was either 0.1:1, 0.5:1, 1.0:1, 2.0:1 or 4.0:1.

The divalent cationic compounds used were $Mg^{++}$, $Zn^{++}$, and $Ca^{++}$ from the salts gluconate and pantothenate. The molar ratios of divalent cationic compounds to anionic amino acids of the hydrolyzed protein were based on the total number of moles of the salt to the total number of moles of the anionic amino acids of the hydrolyzed protein used in the solution. The molar ratios of divalent cationic compounds to anionic amino acids of the hydrolyzed protein set forth in the remaining examples were calculated in the same manner as was described above.

The o-Cl-PPD/MPD-treated hair swatches in the above-mentioned solutions were irradiated in a Weather-Ometer, which is a simulated sunlight exposure machine using a xenon arc lamp, for 5 hours. The o-Cl-PPD/DAPSD treated hair swatches in the above-mentioned solutions were exposed in the Weather-Ometer for 2 hours. The loss of "lightness" (change in L value) and blue color (change in b value) in the treated hair swatches were then determined according to the CIE L*A*B color difference system.

Changes in both L and b values represent color loss due to the irradiation treatment. The results are shown in FIGS. 1a–d. The effective molar ratio range of divalent cationic compounds to anionic amino acids of the hydrolyzed protein that protect the hair from photo damage was from about 0.2:1 to 4.0:1, preferably from about 0.5:1 to 1.0:1, and most preferably at about 0.5:1. Also, compared to hair treated with the hydrolyzed protein only, hair treated with the aforementioned molar ratios of divalent cationic compounds to anionic amino acids showed significantly less color loss.

EXAMPLE 2

Mechanical Strength of Irradiated Hair Treated With Hydrolyzed Protein Alone or in Combination With Divalent Cationic Compounds Samples of normal brown hair were treated for 10 minutes at 40° C. with solutions containing either 25% by weight of hydrolyzed protein from wheat (Cropeptide W) or 25% by weight of hydrolyzed protein from wheat (Cropeptide W) with the divalent cationic compound zinc gluconate, wherein the molar ratio of divalent cationic compound to anionic amino acids of the hydrolyzed protein was about 0.5:1.

Individual samples of treated hair were irradiated in the Weather-Ometer for either 2 hours or 4 hours and then equilibrated at 25° C. at 50% relative humidity for 24 hours. The treated hair was then stretched by the Instron Tester under the same conditions. The Fc value was obtained from the stress/strain curve and represents the condition of the hair. The higher the Fc value, the stronger the hair. This technique is described in U.S. patent application Ser. No. 08/218,565, filed Mar. 28, 1994, and is hereby incorporated by reference in its entirety.

Figure 2:
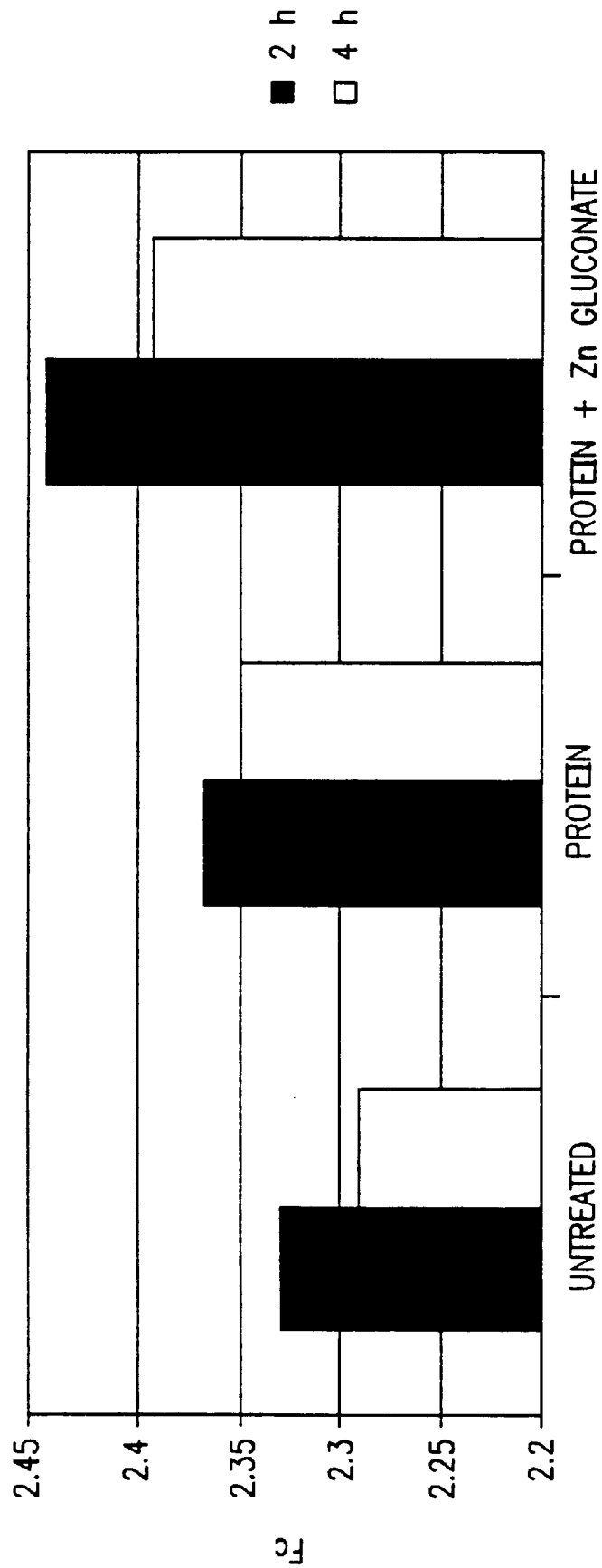
FIG. 2 is a bar graph illustrating the mechanical strength of irradiated hair treated with hydrolyzed protein alone or in combination with divalent cationic compounds.

The results are shown in FIG. 2. Hair treated with the hydrolyzed protein and divalent cationic compound was significantly stronger than hair treated with hydrolyzed protein only, and stronger than the untreated hair. This increase in strength suggests that there may be a synergistic effect between protein and the divalent cationic compound in protecting hair from photo damage.

EXAMPLE 3

Effect of Chlorinated Water on Hair Treated With Hydrolyzed Protein Alone or in Combination With Divalent Cationic Compounds Samples of normal brown hair were treated for 10 minutes at 40° C. with solutions containing either 15% by weight of hydrolyzed protein (Cropeptide W) alone or 15% by weight of hydrolyzed protein (Cropeptide W) with divalent cationic minerals from the salts magnesium gluconate, zinc gluconate and calcium pantothenate. The molar ratio of divalent cationic minerals to anionic amino acids of the hydrolyzed protein was about 0.5:1. This ratio was calculated in the same manner as was described in Example 1.

Samples of treated hair were subjected to the following process up to three times (i.e., three cycles): (a) protein treated; (b) rinsed with water; (c) placed in a 1% NaOCl solution for 10 minutes at room temperature; (d) shampooed using 10% ammonium lauryl sulfate ("ALS") solution; and (e) rinsed with water. Protein loss from the hair was then determined according to the procedure described in the published procedure "A Simple and Sensitive Technique, Based on Protein Loss Measurement, to Assess Surface Damage to Human Hair," *Journal of the Society of Cosmetic Chemists*, Vol. 44, pp. 163–175, (1993).

Figure 3:
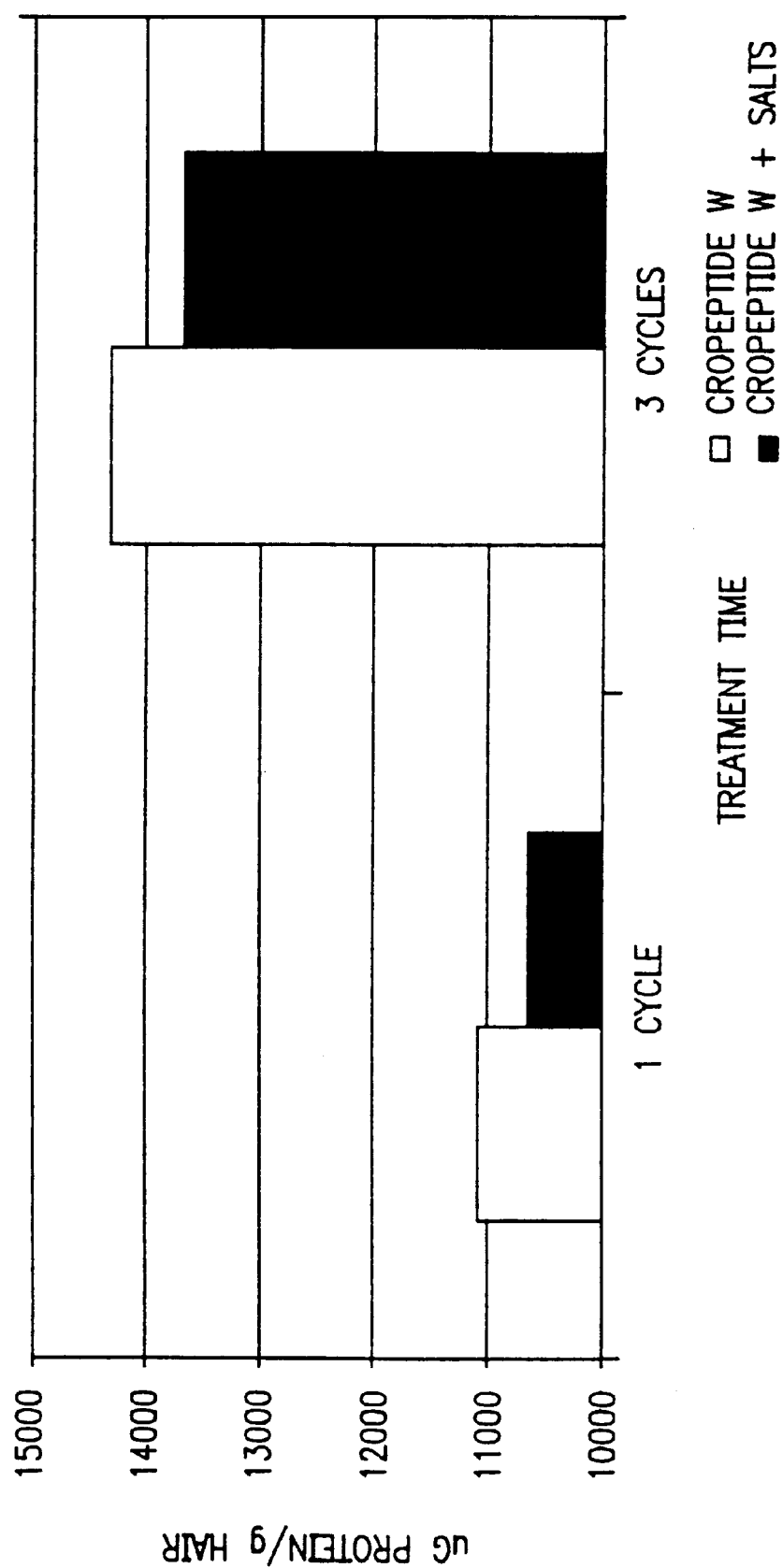
FIG. 3 is a bar graph illustrating the effect of chlorinated water on hair treated with hydrolyzed protein alone or in combination with divalent cationic compounds.

The results are shown in FIG. 3, indicating that the protein loss due to chlorinated water was less in the hair treated with hydrolyzed protein and divalent cationic compounds than in the hair treated with hydrolyzed protein only. This decrease in protein loss suggests that there may be a synergistic effect between the hydrolyzed protein and divalent cationic compounds in protecting hair from oxidative damage caused by chlorinated water.

EXAMPLE 4

Mechanical Strength of Hair Treated With Either Hydrolyzed Protein or Hydrolyzed Protein With Divalent Cationic Compounds After Extended Periods of Irradiation Normal brown hair was treated for 10 minutes at 40° C. with either a solution containing 25% by weight of hydrolyzed protein from wheat (Cropeptide W) or 25% by weight of hydrolyzed protein from wheat (Cropeptide W) together with divalent cationic minerals from the salts magnesium gluconate, zinc gluconate, and calcium pantothenate. The molar ratio of divalent cationic compound to anionic amino acids of the hydrolyzed protein was about 0.5:1.

Samples of the treated hair were irradiated in the Weather-Ometer from 8 hours up to three days. The irradiated hair was then equilibrated at 25° C. at 50% relative humidity for 24 hours and then stretched by the Instron Tester under the same conditions. The Fc value was obtained from the stress/strain curve and represents the condition of the hair, as described in Example 2.

Figure 4:
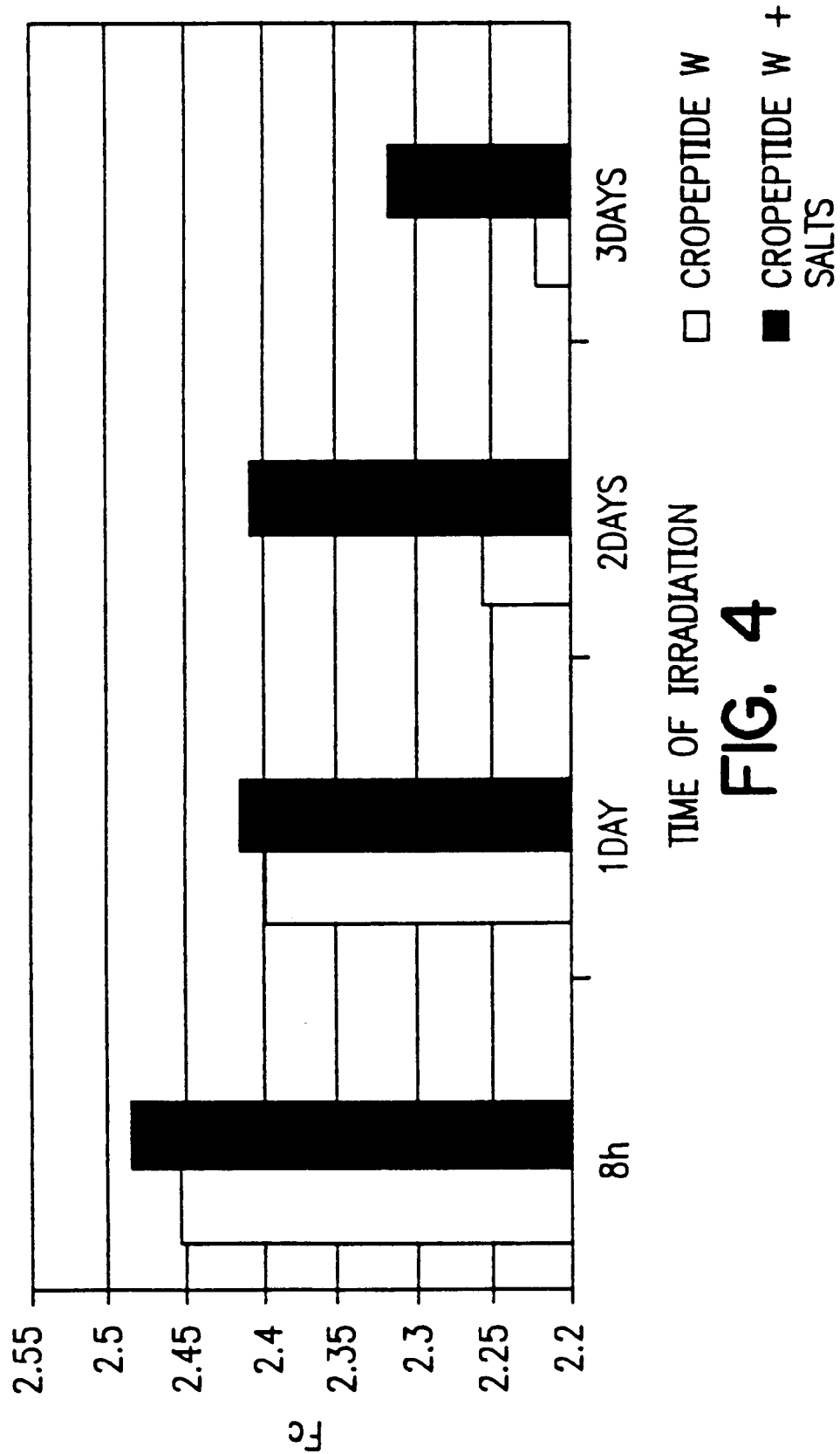
FIG. 4 is a bar graph illustrating the effect of extended periods of irradiation to hair treated with either hydrolyzed protein alone or in combination with divalent cationic compounds.

The results are shown in FIG. 4. The addition of divalent cationic compounds to the hydrolyzed protein solution significantly increased the mechanical strength of the hair, suggesting the presence of a synergistic effect between the hydrolyzed protein and divalent cationic compounds in creating a long lasting protective effect against photo damage.

EXAMPLE 5

Comparison Of The Protective Efficacy of Hydrolyzed Protein From Wheat and Hydrolyzed Protein From Collagen Which Was Either Succinylated or Sulfonated Normal brown hair was individually treated with the following: a) a solution containing 24% by weight of hydrolyzed protein from wheat (Cropeptide W) and divalent cationic compounds from the salts zinc gluconate, magnesium gluconate, and calcium pantothenate; b) a solution containing 25% by weight of succinylated hydrolyzed protein from collagen and divalent cationic compounds from zinc gluconate, magnesium gluconate, and calcium pantothenate; and c) a solution containing 30% by weight of sulfonated hydrolyzed protein from collagen and divalent cationic compounds from the salts zinc gluconate, magnesium gluconate, and calcium pantothenate. The molar ratio of the divalent cationic compounds to the anionic amino acids in the above-mentioned proteins was about 0.2:1. The average molecular weight of succinylated or sulfonated proteins suitable for the present invention may be from 500 up to 500,000 daltons, or more.

Figure 5:
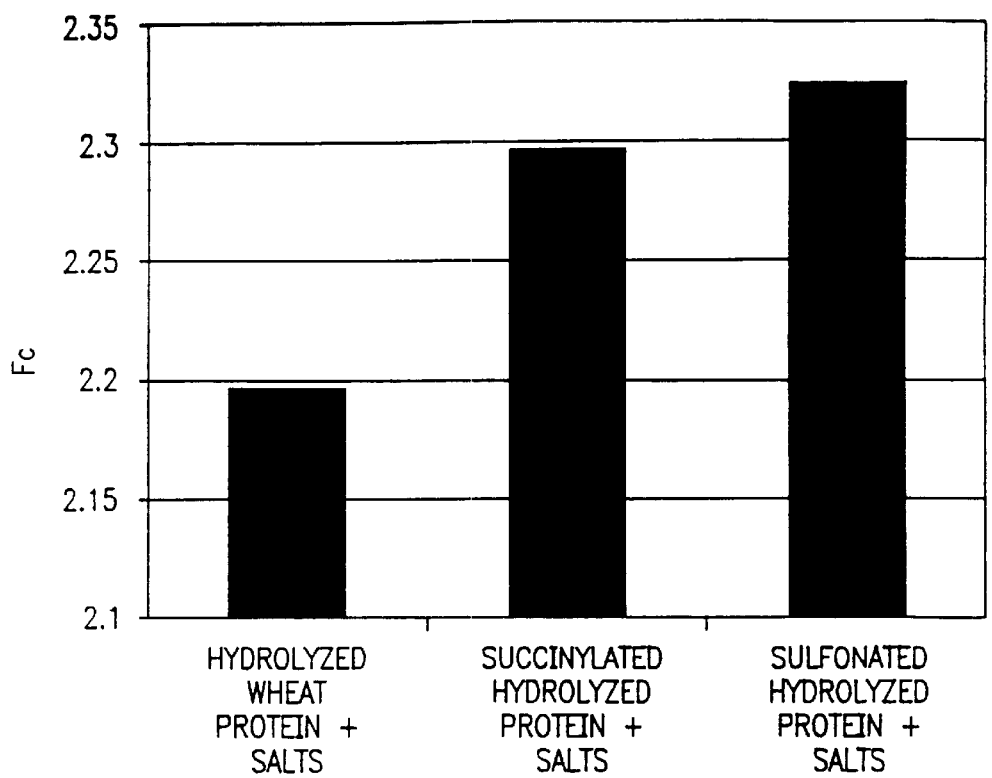
FIG. 5 is a bar graph comparing the protective effects of hydrolyzed protein from wheat and hydrolyzed protein from collagen, which were either succinylated or sulfonated.

The treated hair was irradiated in the Weather-Ometer for 4 hours and then tested by the Instron at 25° C., 50% relative humidity. Based on the stress-strain curve, the condition of the hair was determined according to the Fc values, as described in Example 2. The results are shown in FIG. 5. Compared to the hydrolyzed protein from wheat, the succinylated and sulfonated hydrolyzed protein from collagen both significantly improved the condition of the hair.

EXAMPLE 6

Effect of Combining Vitamin Compounds With A Hydrolyzed Protein and Divalent Cationic Compounds In Protecting Hair From Photo damage Bleached hair swatches were colored with an oxidation dye (o-Cl-PPD/MPD) and then treated for 10 minutes at 40° C. with solutions containing 3% hydrolyzed protein from wheat (Cropeptide W) and 1.8% divalent minerals (Mg Gluconate 0.6%, Zn Gluconate 0.6%, Ca Pantothenate 0.6%). The hair swatches were treated with the above-mentioned solutions with and without 5% Vitamin A or 5% Vitamin E. The molar ratio of the divalent cationic compounds to the anionic amino acids in the hydrolyzed protein in these above-mentioned compositions was about 0.5:1.

The treated hair swatches were irradiated in the Weather-Ometer for 2 hours, and the loss of color (change in the b value) and lightness (change in the L value) was determined according to the CIE L*A*B color difference system. Minimum change in the b value or the L value represents negligible color loss due to the irradiation treatment. The results shown below in Table 2 indicate that adding Vitamin A or Vitamin E to the hydrolyzed protein and divalent cationic compound mixture provided further protection against color loss.

TABLE 2

| | Color Loss Of Irradiated Hair | | |
|---|---|---|---|
| Treatment | Change In b (After 2 Hours) | Change In b (After 4 Hours) | Change In L value (After 2 hours) |
| Protein + Minerals | — | — | 51.1 |
| Protein + Minerals + Vitamin A | — | — | 42.5 |
| Protein + Minerals | 6.12 | 9.49 | — |
| Protein + Minerals + Vitamin E | 0.85 | 1.82 | — |

EXAMPLE 7

Effect of Irradiating Hair Treated With Hydrolyzed Protein, Divalent Cationic Compounds and Vitamin Compounds Normal brown hair was treated for 10 minutes at 40° C. with the following solutions listed in Table 3:

TABLE 3

| Hydrolyzed Protein from Wheat | Minerals | Vitamins | % Residual Cystine | Molar Ratio of Divalent Cationic Compounds to Anionic Amino Acids in Hydrolyzed Protein |
|---|---|---|---|---|
| (1) 24.0 g | — | — | 1.40 | |
| (2) — | — | 5.0 g (Vitamin E) | | |
| (3) 23.0 g | 5.1 g (1.7 g Zn Gluconate 1.7 g Mg Gluconate 1.7 g Ca Pantothenate) | — | 1.34 | 0.6:1 |
| (4) 7.2 g | 5.1 g (1.7 g Zn Gluconate 1.7 g Mg Gluconate 1.7 g Ca Pantothenate) | 5.0 g (1.25 g Vitamin A 1.25 g Vitamin E 1.25 g Vitamin B1 1.25 g Vitamin B6) | 0.42 | 0.6:1 |

The pH range of the compositions described in Table 3 was from about 4 to 6.

The treated hair was irradiated in the Weather-Ometer for 24 hours. The irradiated hair samples were tested by the Instron Tester at 23° C., 50% relative humidity. Based on the stress/strain curves, the Condition Factor (Fc) values were determined using the same procedure described in Example 2 and the percent damage calculated.

Figure 6:
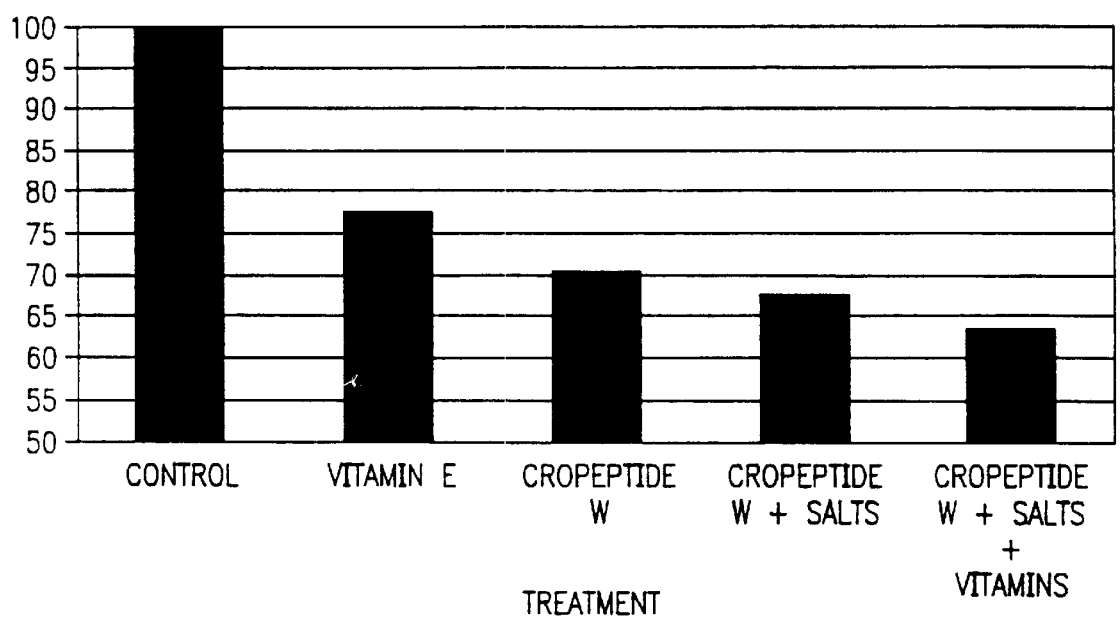
FIG. 6 is a bar graph illustrating the effect of irradiating hair treated with hydrolyzed protein, divalent cationic compounds and vitamin compounds.

The results are shown in FIG. 6. The hydrolyzed protein from wheat (average molecular weight 2500 daltons, molar ratio of anionic to cationic amino acids at about 13.9:1.0, cystine content about 1.40%) provided significant protection from photo damage to the hair.

Further, addition of divalent cationic compounds to the protein solution at about 0.6:1 molar ratio of cationic to anionic amino acids in the hydrolyzed protein (solution (3)) further decreased the damage despite the fact that the protein had a lower protein content (23 grams) and a lower cystine content, 1.34%. Such data is consistent with the theory discussed herein that the hydrolyzed protein is bound to the hair via divalent cationic compound bridges.

Moreover, in the solution (4), wherein the protein content is only 7.2 grams and the protein comprises only 0.42% cystine, an even greater decrease in photo damage was obtained when vitamin compounds were added to the divalent cationic compound/hydrolyzed protein solution, indicating a synergistic effect in combining a divalent cationic compound/hydrolyzed protein with a vitamin compound. This would suggest that compositions comprising hydrolyzed protein, divalent cationic compounds, and vitamins in the proportions according to the present invention impart excellent protection to hair against photo damage.

EXAMPLE 8

Efficacy of Hydrolyzed Protein, Divalent Cationic Compounds and Vitamin Compounds In Retarding Protein Loss From Hair In reference to the shampoo, conditioner and treatment composition described in Table 4, normal brown hair was washed with shampoo for 5 minutes at room temperature, then treated with conditioner for 5 minutes at room temperature. The treatment composition was applied to the conditioned hair for 10 minutes at 40° C., and then placed in a 1% NaOCl solution for 10 minutes at room temperature. Samples of the treated hair were subjected to the shampoo, conditioner, treatment, and NaOCl steps up to 8 times (i.e., 8 cycles). Protein loss from the hair was determined after 2,4 and 8 cycles using the procedure described in Example 3.

TABLE 4

| CFTA Names | Shampoo | Conditioner | Treatment |
| --- | --- | --- | --- |
| Self Emulsifying Glyceryl Ester |  | 6.0% | 6.0% |
| Cetrimonium Chloride |  | 3.5% | 3.5% |
| Dicetyldimonium Chloride |  | 3.0% | 3.0% |
| Hydrolyzed protein from wheat | 0.1% | 0.1% | 3.0% |
| Cetearyl Alcohol |  | 2.0% | 2.0% |
| Trimethylsylyamodimethicone |  | 0.7% | 0.7% |
| Divalent Minerals (Total) | (0.03%) | (0.03%) | (0.75%) |
| Mg Gluconate | 0.01% | 0.01% | 0.25% |
| Zn Gluconate | 0.01% | 0.01% | 0.25% |
| Ca Pantothenate | 0.01% | 0.01% | 0.25% |
| Vitamins (Total) | (0.02%) | (0.02%) | (0.22%) |
| Thiamine Hydrochloride |  |  | 0.1% |
| Pyridoxine Hydrochloride |  |  | 0.1% |
| Tocopheryl Acetate | 0.01% | 0.01% | 0.01% |
| Retinyl Palmitate | 0.01% | 0.01% | 0.01% |
| Menthol |  |  | 0.1% |
| Phytolipid and Hyaluronic Acid |  |  | 0.1% |
| Apricot Seed (Apricot Kernel Powder produced by Alban Muellen, Inc. of Paris, France) |  |  | 0.25% |

TABLE 4-continued

| CFTA Names | Shampoo | Conditioner | Treatment |
| --- | --- | --- | --- |
| Ammonium Lauryl Sulfate | 25% | | |
| Cocamidopropyl Betaine | 10% | | |
| Sodium Lauroyl Sarcosinate | 5% | | |
| Pearlizing Agent | 0.8% | | |
| Methyl Gluceth-20 | 0.25% | | |
| Polyquaternium-4 | 0.1% | | |

The molar ratios of divalent cationic compounds to anionic amino acids of the hydrolyzed protein in both the shampoo and conditioner were about 1:1, and the ratio in the treatment composition was about 0.8:1. The pH range of the above-mentioned compositions was from about 4 to 6.

Figure 7:
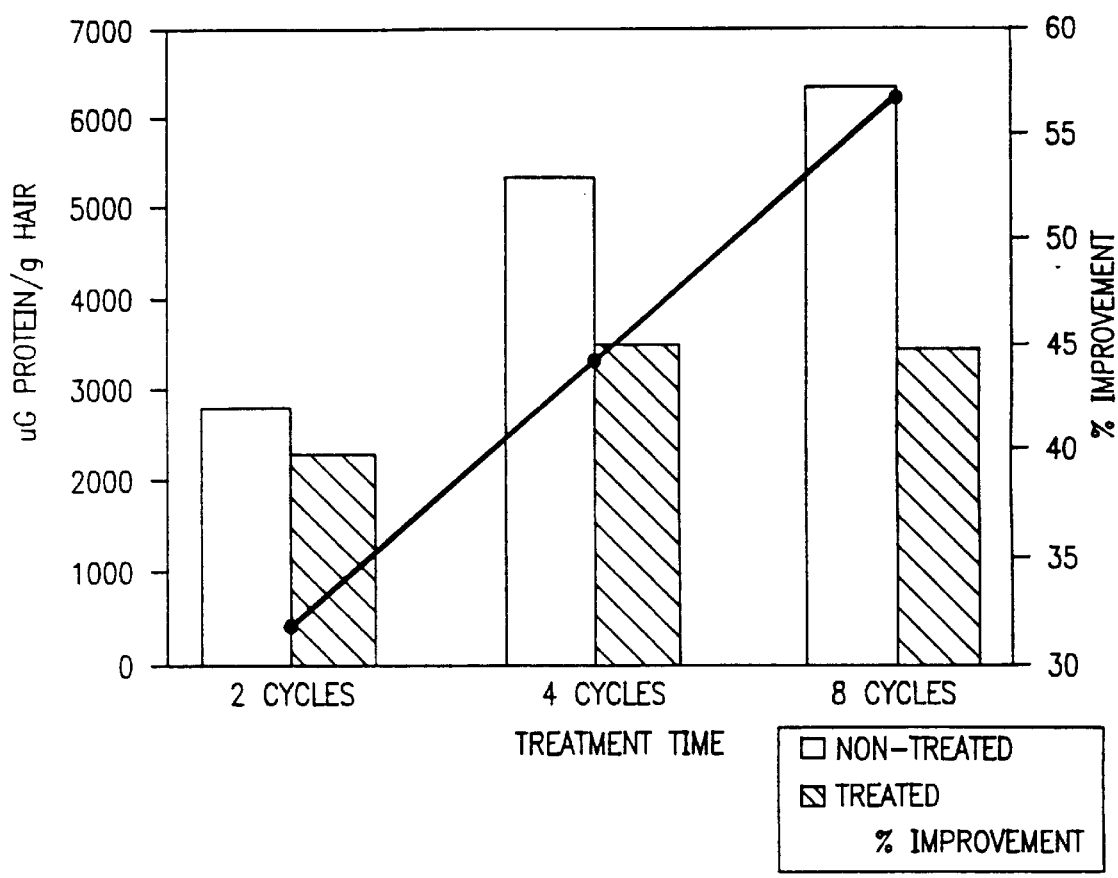
FIG. 7 is a bar graph illustrating the efficacy of hydrolyzed protein, divalent cationic compounds and vitamin compounds in retarding protein loss from hair.

The results are shown in FIG. 7. After 8 cycles, hair treated with the hydrolyzed protein, divalent cationic compound and vitamin compound mixture exhibited about 25% less protein loss due to chlorinated water than the untreated hair.

EXAMPLE 9

Mechanical Strength of Irradiated Hair Treated With Hydrolyzed Protein, Divalent Cationic Compounds and Vitamin Compounds Normal brown hair was treated with the treatment cream described below and irradiated in the Weather-Ometer for 2 hours. The treatment and irradiation steps were repeated up to 7 times (i.e., 7 cycles). After each cycle, the Fc values of the irradiated hair were determined by the Instron Tester, as described in Example 2, at 23° C., 50% relative humidity.

The treatment cream contained the following: Self Emulsifying Glyceryl Ester 6.0%, Cetrimonium Chloride 3.5%, Dicetyldimonium Chloride 3.0%, Hydrolyzed protein from wheat 3.0%, Cetearyl Alcohol 2%, Trimethylsylylamodimethicone 1.0%, Divalent Minerals 1.5% (Mg Gluconate 0.5%, Zn Gluconate 0.5%, and Ca Pantothenate 0.5%), Vitamin Compounds 0.81% (Thiamine Hydrochloride 0.1%, Pyridoxine Hydrochloride 0.5%, Tocopheryl Acetate 0.2%, Retinyl Palmitate 0.01%), Menthol 0.1%, Phytolipid and Hyaluronic Acid 0.1%. The molar ratio of the divalent cationic compounds to anionic amino acids in the hydrolyzed protein was about 1.6:1. The pH range of the composition was from about 4 to 6.

Figure 8:
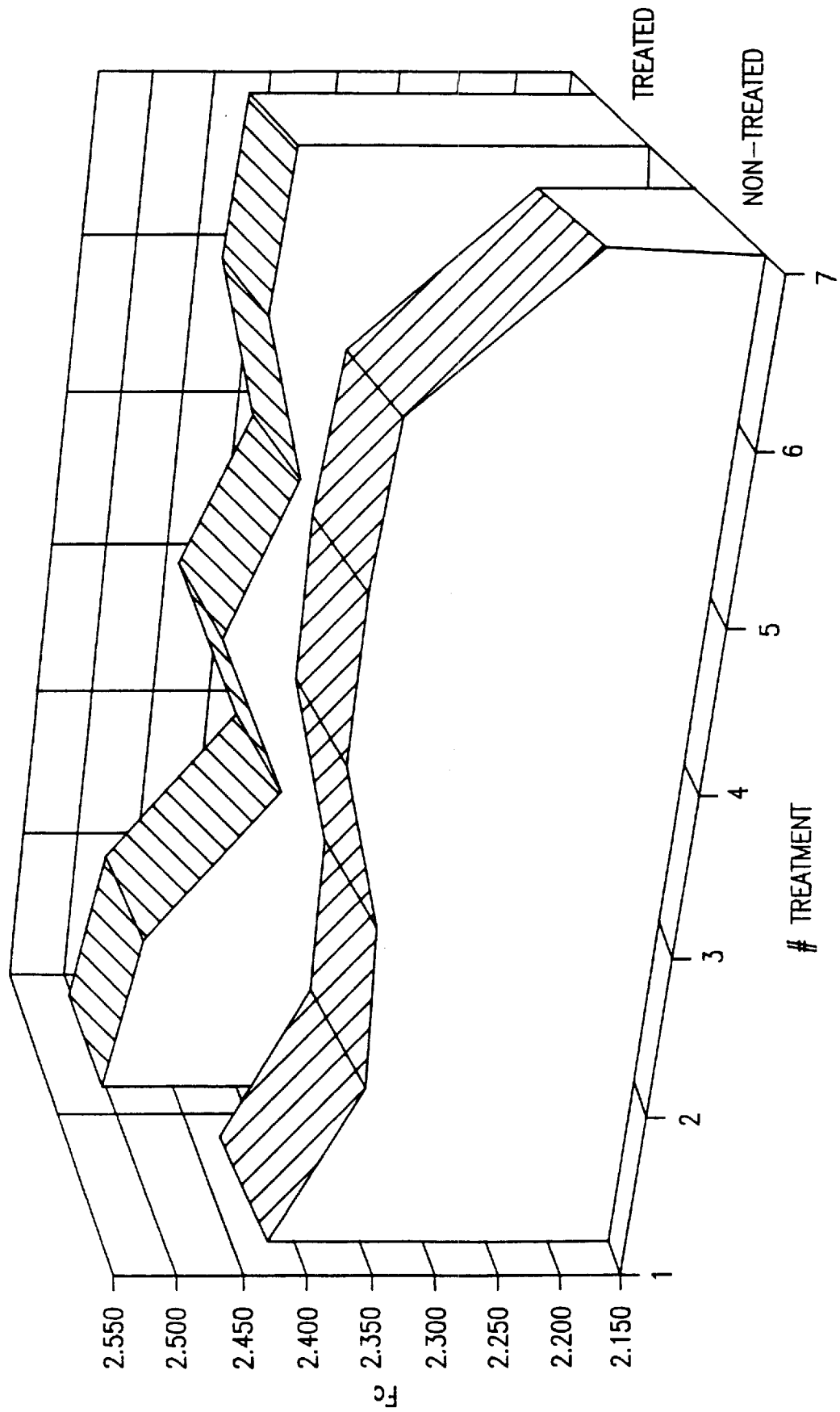
FIG. 8 is a three dimensional graph illustrating the mechanical strength of irradiated hair treated with hydrolyzed protein, divalent cationic compounds and vitamin compounds.

The results are shown in FIG. 8, and indicate that, after each cycle, the condition of the treated hair, as reflected by the higher Fc values, was found to be significantly better than the condition of untreated hair. From this data, it was observed that treating hair with a treatment cream comprising hydrolyzed protein, divalent cationic compounds and vitamin compounds provided substantial protection to the hair from photo damage.

EXAMPLE 10

Efficacy of Hydrolyzed Protein, Divalent Cationic Compounds and Vitamin Compounds In Protecting Hair From Blow Drying and Curling Iron In reference to the shampoo, conditioner and treatment composition described in Table 4, normal brown hair was washed with the shampoo for 5 minutes at room temperature, then treated with the conditioner for 5 minutes at room temperature daily. The treatment composition was applied to the conditioned hair for 10 minutes at 40° C. twice a week. Each day, the hair was blow-dried for 5 minutes and then pressed through a curling iron 50 times. This regimen was carried out for two weeks. The mechanical property of the hair (treated and untreated) was tested by the Instron Tester at 23° C., 50% relative humidity according to the procedure described in Example 2.

The molar ratios of divalent cationic compounds to anionic amino acids of the hydrolyzed protein in both the shampoo and conditioner were about 1:1, and the ratio in the treatment composition was about 0.8:1. The pH range of the above-mentioned compositions was between about 4 and 6.

It was observed that the energy required to break the hair treated with the above-described compositions after the first week was 8% higher than that required to break untreated hair, and 11% higher after two weeks. This would indicate that compositions comprising hydrolyzed protein, divalent cationic compounds, and vitamin compounds in the proportions according to the present invention impart greater protection to the hair against excessive heat by grooming devices, such as blow dryers, curling irons and the like.

EXAMPLE 11

Mechanical Strength of Irradiated and Combed Normal, Bleached and Permed Hair Treated With Hydrolyzed Protein, Divalent Cationic Compounds and Vitamin Compounds In reference to the shampoo, conditioner and treatment in Table 4, bleached hair, permed hair and virgin brown hair were treated with the shampoo for five minutes at room temperature, rinsed with water, treated with the conditioner for 5 minutes at room temperature, rinsed with water and then treated with the hair treatment for 10 minutes at 40° C. The above-mentioned hair samples were treated in this manner twice a week for 14 days. During this time period, the treated hair was irradiated in the Weather-Ometer each day for four hours. Such exposure in the Weather-Ometer is equivalent to 1 day in the sun. Combing (200 strokes) was done on the wet treated hair each day after irradiation. The irradiated and combed hair was tested by the Instron Tester at 23° C., 50% relative humidity, as described in Example 2, to ascertain the Fc value (i.e., mechanical strength of the hair).

Figure 9:
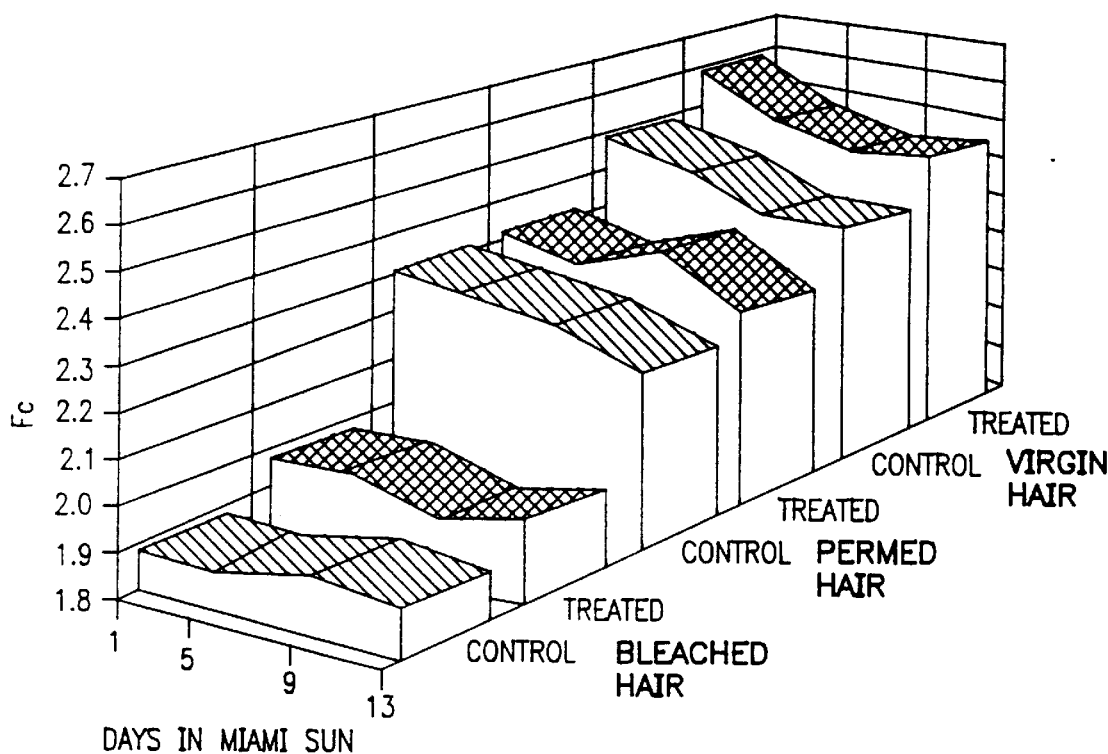
FIG. 9 is a three dimensional graph illustrating the mechanical strength of irradiated and combed normal, bleached and permed hair treated with hydrolyzed protein, divalent cationic compounds and vitamin compounds.

The results are shown in FIG. 9. The higher Fc values indicate that the condition of the hair treated with the shampoo, conditioner and treatment, as described in Table 4, was stronger and in better condition than the untreated hair. This suggests that the hydrolyzed protein/divalent cationic compound/vitamin compound mixture is effective in protecting bleached hair, permed hair, and normal from excessive combing and exposure to sunlight.

Unless otherwise indicated, all weight percentages set forth above refer to the weight percent of the compound based on the total weight of the composition.

Although this invention has been described with reference to specific examples, it will be apparent to one skilled in the art, that various modifications may be made thereto which fall within the scope and preview of the invention.

Various publications are cited herein which are hereby incorporated by reference in their entirety.

EXAMPLE 12

Effective Molar Ratios of Polyamino Cationic Agents to Anionic Amino Acids of the Hydrolyzed Protein FIG. 10 shows test results measuring color loss in untreated hair and hair treated with compositions comprising a negatively charged hydrolyzed protein and polyamino cationic agent in various molar ratios. The testing reflected in FIG. 10 was carried out as follows:

(1) Bleached hair swatches were colored with an oxidation dye, o-Cl-p-Phenylenediamine sulfate/m-Phenylenediamine("o-Cl-PPD/MPD"), and then treated with one of the following solutions for 10 minutes at 40° C.:
 (a) 3% by weight of hydrolyzed protein from soy Hydrosoy 2000 SF;
 (b) 3% by weight of hydrolyzed protein from soy Hydrosoy 2000 SF and cationic amino acid compound. The molar ratio of the cationic amino acid compound to anionic amino acids in the hydrolzyed protein was either 0.1:1, 0.5:1, 1.0:1, 2.0:1 or 4.0:1. Stated another way, the ratio of the amino groups of the cationic amino acid compound to anionic amino acids of the hydrolyzed protein was either 0.2:1, 1.0:1, 2.0:1, 4.0:1 or 8.0:1; and
 (c) water containing an amount of cationic amino acid compound corresponding to that used in each of the solutions described in (b) above.

The cationic amino acid compound used in these tests was arginine hydrochloride (Brand name: L-Arginine Hydrochloride sold by Ajinomoto of Japan). The molar ratio of the cationic amino acid compound to anionic amino acids of the hydrolyzed protein were based on the total number of moles of the arginine to the total number of moles of the anionic amino acids of the hydrolyzed protein used in the solution.

The o-Cl-PPD/MPD-treated hair swatches in the above-mentioned solutions were irradiated in a Weather-Ometer, which is a simulated sunlight exposure machine using a xenon arc lamp, for 5 hours. The loss of "lightness" (change in L value) in the treated hair swatches were then determined according to the CIE L*A*B* color difference between the change in the L value of treated hair and non-treated hair (i.e., hair treated with water alone).

Percentage of improvement represents changes in L which reflects color loss due to the irradiation treatment. Compared to hair treated with the hydrolzyed protein and dibasic amino acid treated with the aforementioned molar ratios of dibasic amino acid compounds to anionic amino acids showed significantly less color loss.

The expected value was determined by adding the separate effects of treating hair with protein and dibasic amino acid compounds alone.

The experimental data in FIG. 10 demonstrate that treatment of hair with a composition comprising the molar ratios of cationic amino acid compounds and hydrolyzed protein yields an unexpected synergistic protective effect in protecting hair.

Based on the experimental data in FIG. 10, treatment of hair with hydrolzyed protein alone resulted in modest protection against photo damage, whereas treatment of hair with a polyamino cationic agent alone yielded minimal or no protection. It was therefore expected that combining the hydrolyzed protein with the polyamino cationic agent would provide little or no additional advantages beyond those obtained with protein alone.

However, as depicted in FIG. 10, the level of protection obtained by treating hair with both protein and polyamino cationic agents in the molar ratios specified in the claims was greater than that achieved when hair was treated with either of the two components alone, and also greater than the expected protection from the additive combination of the hydrolyzed protein with the polyamino cationic agent.

The data in FIG. 10 provides a reasonable indication that the polyamino cationic agents and hydrolyzed proteins disclosed in the specification, when combined in the specified ratios, would provide the same or similar additive effects in protecting hair as the tested polyamino cationic agent and hydrolzyed protein.

EXAMPLE 13

Example of Hair Treatment Compositions Comprising Hydrolyzed Protein and Polyamino Cationic Agents

TABLE 5

SHAMPOO

| CFTA Names | % W/W |
|---|---|
| Water | 67.700 |
| Hydroxypropyl Methylcellulose | 0.400 |
| Methylparaben | 0.100 |
| Ethylparaben | 0.100 |
| Disodium EDTA | 0.100 |
| Taurine | 0.010 |
| Trehalose | 0.001 |
| Arginine HCl | 0.010 |
| D & C Red | >0.001 |
| F D & C Red | >0.001 |
| Lauryldimonium Hydroxypropyl Hydrolyzed Soy Protein | 0.010 |
| Hydrolyzed Soy Protein and Wheat Amino Acid | 0.100 |
| TEA-Lauryl Sulfate | 23.000 |
| Cocamide MIPA | 5.000 |
| SLES and Clycol Distearate and Cocamide MEA, Laureth 10 | 1.500 |
| Na Citrate | 0.500 |
| Citric Acid | 0.400 |
| Phenoxyethanol | 0.500 |
| Fragrance | 0.500 |

TABLE 6

PROTEIN HAIR TREATMENT

| CFTA Name | % W/W |
|---|---|
| Water | 68.00 |
| Hydroxy Ethycellulose | 0.800 |
| Methyl Paraben | 0.200 |
| Ethyl Paraben | 0.100 |
| Disodium EDTA | 0.100 |
| Arginine Hydrochloride | 3 g |
| Taurine | 0.100 |
| Trehalose | 0.001 |
| Hydrolysed Soy Protein | 25.00 |
| Lauryldimonium Hydroxypropyl Hydrolyzed Soy Protein | 0.010 |
| Hydrolysed Soy Protein and Wheat Amino Acid | 0.1000 |
| Polyquaternium II | 0.5000 |
| Cetrimonium Chloride | 1.000 |
| Phenoxyethanol | 0.700 |
| Laureth-23 | 0.150 |
| Phosphoric Acid | 0.200 |

In these compositions, the polyamino cationic agent is arginine hydrochloride. The ratio of the arginine hydrochloride to anionic amino acids of the hydrolyzed protein in the above shampoo and protein hair treatment were about 0.6:1 to 0.9:1. The pH range of these compositions was from about 4 to 6. The above compositions would provide a greater additive effect in protecting hair than the combined individual effects of the same or similar compositions containing the hydrolyzed protein or polyamino cationic agent alone.

Various publications are cited herein, the contents of which are hereby incorporated by reference in their entireties.

We claim:

1. A cosmetic composition for treating hair comprising:

a. from about 0.1 to 50% by weight of a hydrolyzed protein comprising anionic and cationic amino acids, wherein the molar ratio of the anionic amino acids to cationic amino acids of the hydrolyzed protein is at least 2.1:1.0, wherein the hydrolyzed protein comprises at least 0.25% by weight of cysteine, cystine or any combination thereof, and wherein the hydrolyzed protein has an average molecular weight of less than 500,000 daltons;

b. a polyamino cationic agent, wherein the polyamino cationic agent is a cationic amino acid compound having a plurality of amino groups, wherein said amino acid compound is selected from the group consisting of histidine, arginine, lysine, hydroxylysine, ornithine or combinations thereof, wherein the ratio of the amino groups of the cationic amino acid compound to the anionic amino acids of the hydrolyzed protein is from about 0.2:1 to 2:1; and c. from about 1 to 99.9% by weight of cosmetic carrier.

2. A cosmetic composition for treating hair comprising:

a. from about 0.1 to 50% by weight of a hydrolyzed protein comprising anionic and cationic amino acids, wherein the molar ratio of the anionic amino acids to cationic amino acids of the hydrolyzed protein is at least 2.1:1.0, wherein the hydrolyzed protein comprises at least 0.25% by weight of a sulphur-containing amino acid, and wherein the hydrolyzed protein has an average molecular weight of less than 500,000 daltons;

b. a polyamino cationic agent, wherein the cationic polyamino agent is a peptide, wherein at least 2 of the amino acids of the peptide are cationic amino acid compounds selected from the group consisting of histidine, arginine, lysine, hydroxylysine, ornithine or combinations thereof; wherein the ratio of the amino groups of the peptide to the anionic amino acids of the hydrolyzed protein is from about 0.2:1 to 2:1; and c. from about 1 to 99.9% by weight of cosmetic carrier.

3. A cosmetic composition for treating hair comprising:

a. from about 0.1 to 50% by weight of a hydrolyzed protein comprising anionic and cationic amino acids, wherein the molar ratio of the anionic amino acids to cationic amino acids of the hydrolyzed protein is at least 1.1:1.0, wherein the hydrolyzed protein comprises at least 0.25% by weight of a sulphur-containing amino acid, and wherein the hydrolyzed protein has an average molecular weight of less than 500,000 daltons;

b. a polyamino cationic agent having the formula:

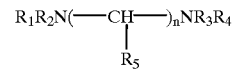

where n=1–6 and $R_1$, $R_2$, $R_3$, $R_4$, and $R_5$ are selected from the group consisting of H, an alkyl group or compound comprising one or more amino groups, wherein the molar ratio of the amino groups of the polyamino cationic agent to the anionic amino acids of the hydrolyzed protein is from about 0.2:1 to 2:1;

c. from about 1 to 99.9% by weight of cosmetic carrier.

4. The hair treatment composition according to claim 3, wherein the polyamino cationic agent is a diamino compound having the formula:

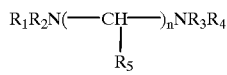

where n=1–6 and $R_1$, $R_2$, $R_3$, $R_4$, and $R_5$ are selected from the group consisting of H, or an alkyl group.

5. The hair treatment composition according to claim 1, 2, 3 or 4 wherein the molar ratio of the anionic amino acids to cationic amino acids of the hydrolyzed protein is from about 2.1:1 to 15:1.

6. The hair treatment composition according to claim 1, 2, 3, or 4 wherein the ratio of the amino groups of the polyamino cationic agent to the anionic amino acids of the hydrolyzed protein is from about 1:1 to 2:1.

7. The hair treatment composition according to claim 1, 2, 3, or 4 wherein the ratio of the amino groups of the polyamino cationic agent to anionic amino acids of the hydrolyzed protein is about 1.0:1.

8. The hair treatment composition according to claim 1, 2, 3, or 4 wherein the source of the hydrolyzed protein is selected from the group consisting of wheat, milk, keratin, soy, collagen or mixtures thereof.

9. The hair treatment composition according to claim 1, 2, 3, or 4 further comprising 0.01 to about 5% by weight of a vitamin compound selected from the group consisting of vitamins having antioxidant properties and vitamins which absorb ultraviolet light within the wavelength region between 290 nm and 420 mn.

10. The hair treatment composition according to claim 9, wherein the vitamin compound is selected from the group consisting of: (1) Vitamin A, an esterfied form of Vitamin A and salt form of Vitamin A; (2) Vitamin B1, an esterfied form of Vitamin B1 and a salt form of Vitamin B1; (3) Vitamin $B_6$, an esterfied form of Vitamin $B_6$ and a salt form of Vitamin $B_6$; (4) Vitamin E, an esterfied form of Vitamin E and a salt form of Vitamin E; (5) Beta-Carotene, an esterfied form of Beta-Carotene and a salt form of Beta-Carotene; (6) Vitamin $B_3$, Vitamin $B_5$, Vitamin $B_{12}$, Vitamin C, Vitamin $D_2$, Vitamin $D_3$, Vitamin F, Vitamin $K_1$, and their esterfied forms and salt forms; and (7) Retinyl Palmitate, Thiamine Nitrate, Thiamine Phosphoric Acid Ester, Niacinamide Ascorbate, Pyridoxine Dilaureate, Pyridoxine Dioctenoate, Pyridoxine Dipalmitate, Pyridoxine Tripalmitate, Ascorbyl Palmitate, Ascorbyl Glucoseamine, Ascorbyl Dipalmitate, Ascorbyl Stearate, Tocopheryl Acetate, Tocopheryl Linoleate, Tocopheryl Nicotinate, Tocopheryl Succinate.

11. The hair treatment composition according to claim 1, wherein the polyamino cationic acid compound comprises a salt selected from the group consisting of hydrochloride, hydrochloride monohydrate, monohydrochloride monohydrate, methyl ester dihydrochloride, ethyl ester dihydrochloride, dihydrochloride, or combinations thereof.

12. The hair treatment composition according to claim 2, wherein the peptide consists essentially of 2 amino acids, where said 2 amino acids are cationic amino acid compounds.

13. The hair treatment composition according to claim 12, wherein the cationic amino acid compounds are selected from the group consisting of histidine, arginine, lysine, hydroxylysine, ornithine or any combination thereof.

14. The hair treatment composition according to claim 1, 2, 3, or 4 wherein the pH of the composition is about 3.5 to 10.

15. A method for treating hair comprising applying to the hair the compositions of claims 1, 2, 3 or 4.

* * * * *

UNITED STATES PATENT AND TRADEMARK OFFICE
CERTIFICATE OF CORRECTION

PATENT NO. : 6,013,250

DATED : JAN. 11, 2000

INVENTOR(S) : CANNELL ET AL.

It is certified that error appears in the above-identified patent and that said Letters Patent is hereby corrected as shown below:

COVER PAGE:

"15 Claims," should read -- 14 Claims, --.

IN THE DESCRIPTION:

Column 9, line 2: "Omithine" should read -- Ornithine --.

Column 14, line 64: "4to 6." should read -- 4 to 6. --.

Column 20, claim 1, line 5: following "protein" insert -- from keratin, soy, milk, collagen or wheat, said hydrolyzed protein--;

line 8: "cysteine, cystine or any" should read -- a sulfur-containing amino acid--;

line 9: "combination thereof" should be deleted;

lines 13 and 14: "agent, wherein the polyamino cationic agent is" should read --agent consisting of--;

lines 14, 16 and 19: "compound" should be deleted.

UNITED STATES PATENT AND TRADEMARK OFFICE
CERTIFICATE OF CORRECTION

PATENT NO. : 6,013,250
DATED : Jan. 11, 2000
INVENTOR(S) : Cannell et al.

It is certified that error appears in the above-identified patent and that said Letters Patent is hereby corrected as shown below:

Column 20, claim 2, line 25: following "protein" insert --from keratin, soy, milk, collagen or wheat, said hydrolyzed protein--;
lines 32-36: "agent, wherein the cationic polyamino agent is a peptide, wherein at least 2 of the amino acids of the peptide are cationic amino acid compounds" should read --agent consisting of a peptide of 2 to 100 amino acids having a net cationic charge of 2 or greater than 2, wherein at least 2 of the amino acids of the petide are cationic amino acids having a plurality of amino groups--.

Column 20, claim 3, line 47: "1.1:1.0," should read -- 2.1:1.0, --;
line 51: following "agent" insert --consisting of a diamino compound--;
lines 59-63: "an alkyl group or compound comprising one or more amino groups, wherein the molar ratio of the amino groups of the polyamino cationic agent to the anionic amino acids of the hydrolyzed protein is from about 0.2:1 to 2:1;" should read --or an alkyl group, wherein the molar ratio of the amino groups of the diamino compound to the anionic amino acids of the hyrolyzed protein is about 0.2:1 to 2:1;--;

Column 20, claim 4, line 65 through column 21, line 7: Delete claim 4 in its entirety Columns 21 and 22, claims Nos. 5, 6, 7, 8, 9, 10, 11, 12, 13, 14, and 15:
Renumber these claims as claims Nos. 4, 5, 6, 7, 8, 9, 10, 11, 12, 13 and 14, respectively Column 21, claim 5 (now renumbered as claim 4), line 2: "3 or 4" should read -- or 3 --.

Column 21, claims 6, 7 and 9 (now renumbered 5, 6, and 8): "3, or 4" in the second line of each claim should read -- or 3 --.

Column 21, claim 8 (now renumbered as claim 7), lines 20-21: "1, 2, 3 or 4" should read -- 3 --.

UNITED STATES PATENT AND TRADEMARK OFFICE
CERTIFICATE OF CORRECTION

PATENT NO. : 6,013,250
DATED : Jan. 11, 2000
INVENTOR(S) : Cannell et al.

It is certified that error appears in the above-identified patent and that said Letters Patent is hereby corrected as shown below:

Column 21, claim 9 (now renumbered as claim 8), line 27: "vitamins", second occurrence, should be deleted.

Column 21, claim 10 (now renumbered as claim 9), line 30: "9," should read -- 8, --.

Column 22, claim 13 (now renumbered as claim 12), line 1: "12," should read "11,";
line 26: "acid compounds" should read -- acids --.

Column 22, claim 14 (now renumbered as claim 13), line 30: "2, 3, or 4" should read -- 2, or 3 --.

Column 22, claim 15 (now renumbered as claim 14) line 33: "1, 2, 3, or 4" should read -- 1, 2, or 3 --.

Signed and Sealed this

Twenty-ninth Day of May, 2001

NICHOLAS P. GODICI

*Attest:*

*Attesting Officer*　　　Acting Director of the United States Patent and Trademark Office